(12) United States Patent
Sutkin et al.

(10) Patent No.: US 9,821,122 B2
(45) Date of Patent: *Nov. 21, 2017

(54) HANDHELD MEDICAL SUBSTANCE DISPENSING SYSTEM, APPARATUS AND METHODS

(71) Applicant: Accunit, LLC, Los Altos, CA (US)

(72) Inventors: Howard S. Sutkin, Los Gatos, CA (US); Jerry Botkin, Crown Point, IN (US)

(73) Assignee: Accunit, LLC, Los Altos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/798,008

(22) Filed: Jul. 13, 2015

(65) Prior Publication Data

US 2016/0038687 A1 Feb. 11, 2016

Related U.S. Application Data

(63) Continuation of application No. 14/286,701, filed on May 23, 2014, now Pat. No. 9,114,216, which is a
(Continued)

(51) Int. Cl.
*A61M 5/315* (2006.01)
*A61M 5/31* (2006.01)
*A61M 5/32* (2006.01)

(52) U.S. Cl.
CPC .... *A61M 5/31581* (2013.01); *A61M 5/31526* (2013.01); *A61M 5/3287* (2013.01);
(Continued)

(58) Field of Classification Search
CPC ................ A61M 5/31581; A61M 5/00; A61M 2005/3152; A61M 25/0147; A61M 5/008
(Continued)

(56) References Cited

U.S. PATENT DOCUMENTS

| 62,955 A | 3/1867 | Hammond |
|---|---|---|
| 780,147 A | 1/1905 | Wilcox et al. |

(Continued)

FOREIGN PATENT DOCUMENTS

| JP | 03055067 | 3/1991 |
|---|---|---|
| WO | WO 2012/089445 | 7/2012 |
| WO | WO 2013/160680 | 10/2013 |

*Primary Examiner* — Phillip Gray
(74) *Attorney, Agent, or Firm* — Levine Bagade Han LLP

(57) ABSTRACT

Various handheld medical dispensing configurations and methods including the following: Handheld medical dispensing system comprises a syringe, which has a plunger, releasably mounted to syringe actuation apparatus, the apparatus having an actuator configured such that it can move the plunger more than once to dispense a plurality of amounts of substance from the syringe. A method of dispensing fluid from a syringe comprises holding a medical substance delivery system including a syringe, which has a needle, and which is secured to syringe actuation apparatus configured to dispense predetermined amounts of the substance from the syringe, penetrating the needle at one patient site and using the apparatus to deliver a predetermined amount of the substance, and penetrating the needle at another patient site and using the apparatus to deliver a predetermined amount of the substance.

18 Claims, 14 Drawing Sheets

Related U.S. Application Data continuation-in-part of application No. 13/550,473, filed on Jul. 16, 2012.

(52) U.S. Cl.
CPC ....... *A61M 5/3148* (2013.01); *A61M 5/31586* (2013.01); *A61M 2005/3112* (2013.01)

(58) Field of Classification Search
USPC .................................. 604/218, 209, 224, 181
See application file for complete search history.

(56) References Cited

U.S. PATENT DOCUMENTS

| | | | |
|---|---|---|---|
| 2,221,739 | A | 11/1940 | Reiter |
| 2,472,116 | A | 6/1949 | Maynes |
| 2,491,978 | A * | 12/1949 | Helfman ............... A61M 5/00 604/181 |
| 2,725,877 | A | 12/1955 | Reiter et al. |
| 2,892,457 | A | 6/1959 | Sturtz |
| 3,395,704 | A | 8/1968 | Frey et al. |
| 3,720,211 | A | 3/1973 | Kyrias |
| 4,444,560 | A | 4/1984 | Jacklich |
| 4,465,478 | A | 8/1984 | Sabelman et al. |
| 4,512,769 | A | 4/1985 | Kozam et al. |
| 4,710,178 | A | 12/1987 | Henri et al. |
| 4,883,472 | A | 11/1989 | Michel |
| 5,004,124 | A | 4/1991 | Stefaniak et al. |
| 5,022,563 | A | 6/1991 | Marchitto et al. |
| 5,115,816 | A | 5/1992 | Lee |
| 5,279,579 | A | 1/1994 | D'Amico |
| 5,336,201 | A | 8/1994 | von der Decken |
| 5,433,352 | A | 7/1995 | Ronvig |
| 5,507,727 | A | 4/1996 | Crainich |
| 5,536,249 | A | 7/1996 | Castellano et al. |
| 5,540,657 | A | 7/1996 | Kurjan et al. |
| 5,611,784 | A | 3/1997 | Barresi et al. |
| 5,692,642 | A | 12/1997 | Brattesani |
| 5,735,437 | A | 4/1998 | Broyles et al. |
| 5,743,431 | A | 4/1998 | Brattesani |
| 6,471,098 | B1 | 10/2002 | Shiau |
| 6,599,272 | B1 | 7/2003 | Hjertman et al. |
| 6,607,512 | B2 | 8/2003 | Oliver et al. |
| 7,011,234 | B2 | 3/2006 | Stradella |
| 7,041,084 | B2 | 5/2006 | Fojtik |
| 7,476,216 | B2 | 1/2009 | Takatsuka et al. |
| 7,563,253 | B2 | 7/2009 | Tanner et al. |
| 7,678,084 | B2 | 3/2010 | Judson et al. |
| 7,708,732 | B2 | 5/2010 | Norrie et al. |
| 7,794,432 | B2 | 9/2010 | Young et al. |
| 7,800,147 | B2 | 9/2010 | Adkisson et al. |
| 7,922,699 | B2 | 4/2011 | Baba et al. |
| 8,123,084 | B2 | 2/2012 | Reynolds et al. |
| 8,535,268 | B2 | 9/2013 | Auld et al. |
| 8,708,971 | B2 | 4/2014 | Segal |
| 8,920,374 | B2 | 12/2014 | Bokelman et al. |
| 8,992,481 | B2 | 3/2015 | Mudd et al. |
| 9,114,216 | B2 | 8/2015 | Sutkin et al. |
| 2005/0085767 | A1 | 4/2005 | Menassa |
| 2006/0069355 | A1 | 3/2006 | Judson et al. |
| 2007/0233038 | A1 | 10/2007 | Pruitt et al. |
| 2008/0058732 | A1 | 3/2008 | Harris |
| 2009/0124996 | A1 | 5/2009 | Heneveld et al. |
| 2009/0254046 | A1 | 10/2009 | Hetherington |
| 2009/0299328 | A1 | 12/2009 | Mudd et al. |
| 2010/0305501 | A1 | 12/2010 | Ratjen |
| 2011/0028910 | A1 | 2/2011 | Weber |
| 2011/0030191 | A1 | 2/2011 | Weill et al. |
| 2011/0137286 | A1 | 6/2011 | Mudd et al. |
| 2011/0270197 | A1 | 11/2011 | Weill et al. |
| 2012/0265143 | A1 | 10/2012 | Krumme et al. |
| 2013/0006215 | A1 | 1/2013 | Sharratt et al. |
| 2013/0072878 | A1 | 3/2013 | Avery |
| 2013/0296778 | A1 | 11/2013 | Damgaard-Soerensen et al. |
| 2014/1001770 | | 1/2014 | Sutkin et al. |
| 2014/0257241 | A1 | 9/2014 | Sutkin et al. |
| 2014/0323984 | A1 | 10/2014 | Bruce et al. |
| 2014/0343490 | A1 | 11/2014 | Kanner et al. |
| 2015/0157802 | A1 | 6/2015 | Yoon |
| 2015/0182702 | A1 | 7/2015 | Sutkin et al. |
| 2016/0120751 | A1 | 5/2016 | Mounce et al. |

* cited by examiner

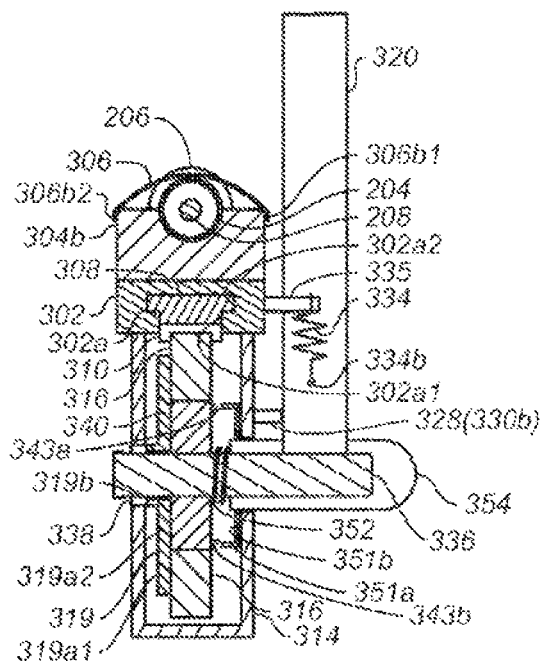
FIG. 7A
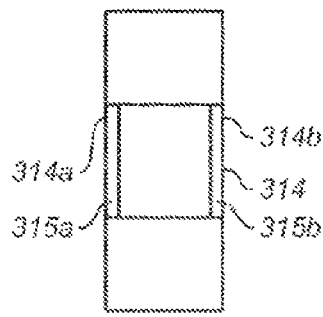
FIG. 7B
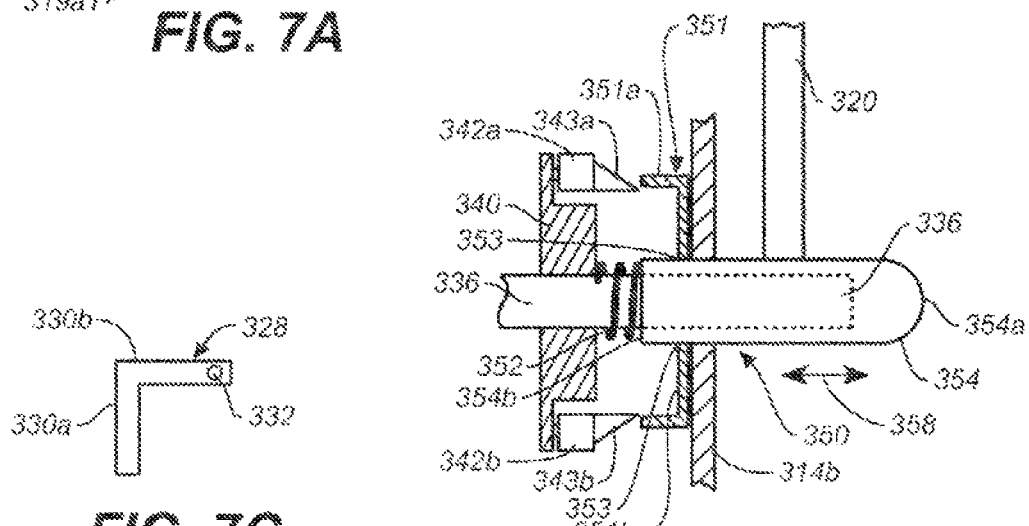
FIG. 7D
FIG. 7C
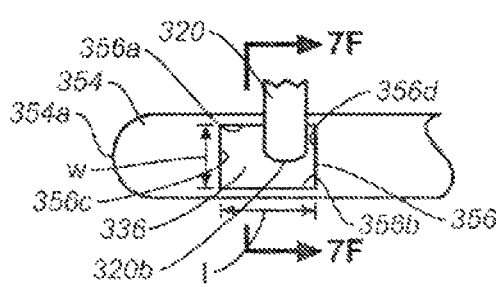
FIG. 7E
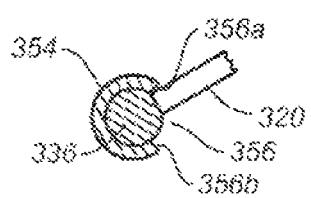
FIG. 7F

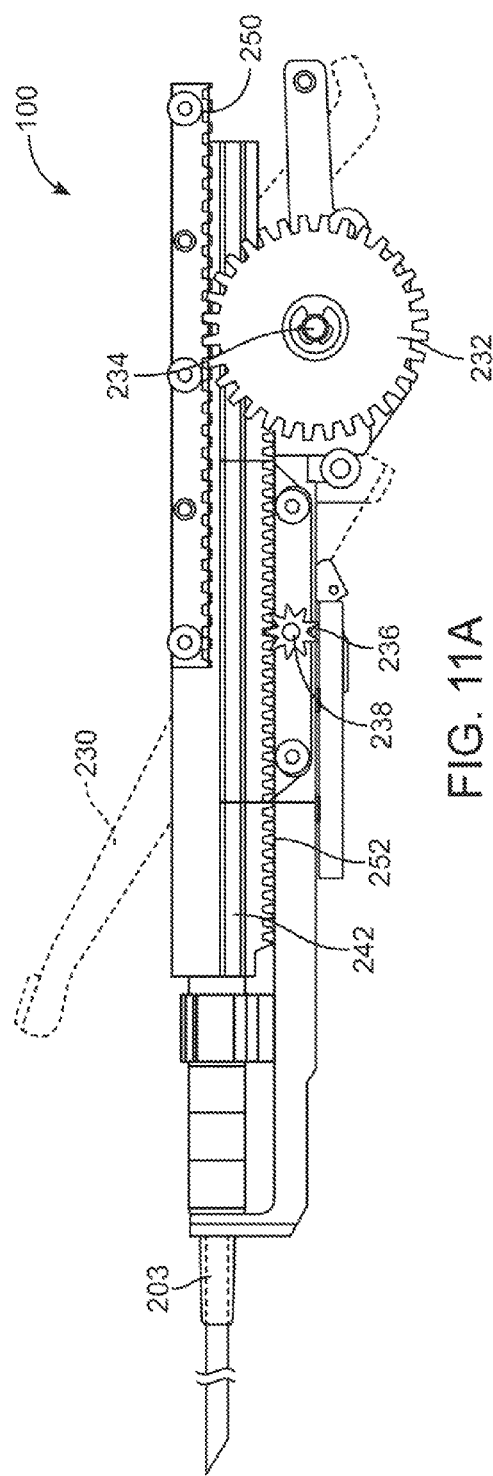
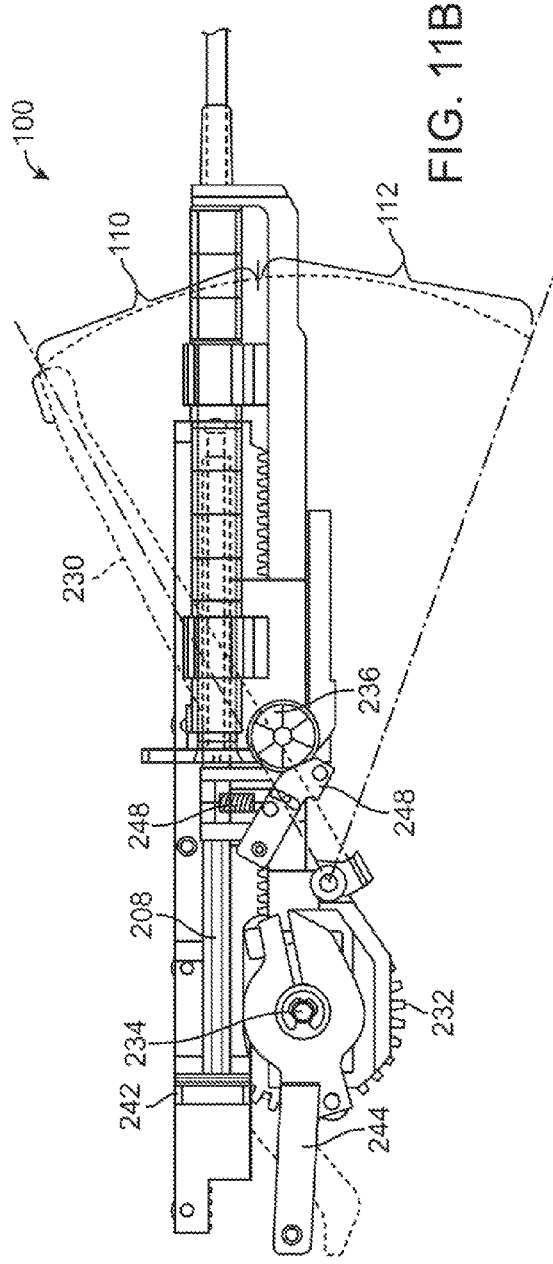

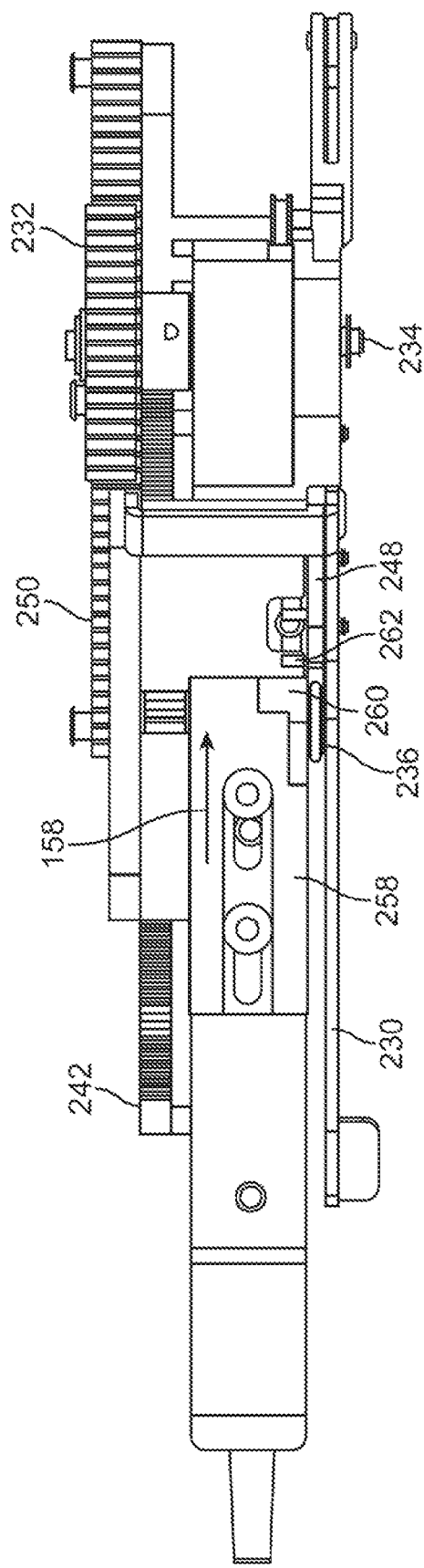

HANDHELD MEDICAL SUBSTANCE DISPENSING SYSTEM, APPARATUS AND METHODS

RELATED APPLICATIONS

This application is a continuation of U.S. patent application Ser. No. 14/286,701 filed May 23, 2014, which is a continuation-in-part of U.S. application Ser. No. 13/550,473 filed Jul. 16, 2012, the contents of which are incorporated herein by reference in their entirety.

BACKGROUND OF THE INVENTION

In the field of plastic surgery, non-invasive procedures have enjoyed increasing popularity over the past ten years. The most common procedures include injection of liquid fillers in facial lines and wrinkles as well as the use of agents which paralyze selective muscles of the face in order to provide diminishment and smoothing of wrinkles. Typically, a dermal filler or paralytic agent such as Botox® Cosmetic (onabotulinumtoxinA), is used on a recurrent outpatient basis. Such agents typically are available in sterile vials of product in freeze-dried form. The clinician will reconstitute the preparation according to a specific recipe of sterile saline (fluid) added to the vial of product. Once mixed, the preparation is drawn up into a syringe, for subdermal delivery using a small bore medical needle. The most common delivery method uses a one cc disposable syringe which is fitted with a disposable needle. Importantly, small, reproducible allotments of the fluid are delivered via multiple injections into the muscles of the face, such as the frontalis muscle in a field of the face which would benefit from treatment.

Further, it is well known that the use of a small syringe during injections of the face on a subject who is sitting in a chair is generally uncomfortable for the health care provider and subject to unsteady maneuvering of the syringe due to the necessity of pushing on the plunger which is located at the rear end of the syringe assembly, while trying to hold the syringe steady. Accordingly, there remains a need to provide a handheld dispenser or syringe that can be more stable or desired tiller or fluid amounts from a handheld dispenser or syringe in such applications in order to provide predictable and/or desired results.

SUMMARY OF THE INVENTION

The present invention involves improvements in medical substance delivery systems and can be used in the delivery of any substance. One such example includes a medicinal substance delivery systems for the treatment of facial lines and/or wrinkles.

One variation of the device disclosed herein includes a dispensing unit for use with a syringe. For example, such a device can include a syringe having a barrel, and a plunger slidable relative to the barrel to dispense substances located therein, the medical dispensing system comprising a housing assembly being configured to secure the barrel of the plunger such that a distal end of the barrel is adjacent to a distal end of the housing assembly; a drive mechanism coupled to the housing assembly, the drive mechanism comprising a plunger fitting that engages the plunger; an actuator; and a gear drive assembly being coupled between the plunger fitting and the actuator, the gear drive assembly being configured to move in response to movement of the actuator to produce movement of the plunger fitting in a first direction relative to the distal end of the housing and subsequently in a second direction that is opposite to the first direction.

Variations of the dispensing unit include a gear drive assembly that moves the plunger fitting in the first direction and subsequently in the second direction in a single stroke of the actuator. Additionally, in certain variations a portion of the gear drive assembly can be disengaged such that the plunger fitting moves in the second direction in a single stroke of the actuator.

As noted herein, the dispensing units disclosed herein can include a gear drive assembly that comprises at least a first gear structure configured to produce movement of the plunger fitting in the first direction and a second gear structure configured to produce movement of the plunger fitting in the second direction; and where a single stroke of the actuator comprises a first segment and a second segment, where movement of the actuator in the first segment causes movement of the first gear structure and movement of the actuator in the second segment causes movement of the second gear structure. In additional variations, the gear drive assembly disengages the first gear structure during movement of the actuator in the second segment.

As discussed herein, variation of the dispensing units can employ one or more rack and pinion gear assemblies. However, any such mechanism can be used to achieve the same results.

Examples of the dispensing units include one or more first gear structures that are releasably coupled to an actuator through a first shaft such that movement of the actuator through the first segment to the second segment causes de-coupling of the first shaft and the actuator. In an additional variation, a second gear structure can be disengaged from the actuator until the actuator moves through the first segment.

In another variation, a dispensing unit can include a syringe, the syringe having a barrel, and a plunger slidable relative to the barrel to dispense substances located therein; a housing assembly being configured to secure the barrel of the plunger such that a distal end of the barrel is adjacent to a distal end of the housing assembly; a drive mechanism coupled to the housing assembly, the drive mechanism comprising a plunger fitting that engages the plunger; and an actuator; and a gear drive assembly being coupled to the plunger fitting and the actuator, the gear drive assembly being configured to move in response to movement of the actuator to produce movement of the plunger fitting in a first direction relative to the distal end of the housing and subsequently in a second direction that is opposite to the first direction.

The present disclosure also includes methods for injecting a substance into a patient. In one example the method includes positioning a syringe adjacent to a tissue site of the patient, the syringe having a plunger coupled to a barrel and a cannula extending from the barrel; advancing the cannula into the tissue site; actuating a drive mechanism coupled to the syringe where the drive mechanism is configured to move the plunger and barrel relative to each other in a first direction and subsequently in a second direction that is opposite to the first direction upon a single directional actuation of an actuator of the drive mechanism.

In another variation, the methods can include methods of administering an injection of a substance into a patient, by, for example, positioning an injection apparatus adjacent to a tissue site of the patient, the injection apparatus having a reservoir with a plunger slidable therein and a cannula extending from the barrel; advancing the cannula into the tissue site; single-handedly actuating a lever to first cause the plunger to increase a volume of the reservoir and subsequently to cause the plunger to decrease the volume of the reservoir to deliver the substance into the patient.

Another variation of a device according to the present invention includes a device for delivering an injection of a substance into a tissue region, where the device comprises a reservoir configured to retain the substance; a plunger coupled to the reservoir such that movement of the plunger changes a volume of the reservoir; a cannula fluidly coupled to the reservoir at a distal end, the cannula configured to penetrate into the tissue region; an actuator mechanically coupled to the plunger where the actuator is configured to move from a rest position to a delivery position, where partial movement of the actuator from the rest position produces movement of the plunger in a first direction and where continued movement of the actuator towards the delivery position produces movement of the plunger in a second direction, where the first direction is opposite to the second direction.

Any feature or features of any embodiment or variation can be combined with any feature or features of another embodiment or variation whether preferred or not. For example, any of the embodiments or variations can have any one or combination of the following features: a syringe plunger and actuation apparatus with an actuator to move the syringe plunger more than once to dispense a plurality of amounts (or volumes) of substance; a fastener to fasten the syringe to the syringe actuation apparatus; a syringe with a needle; a syringe plunger and an actuator that includes a pusher to push the syringe plunger; an actuator that includes a drive or drive assembly coupled to a syringe plunger pusher to drive the pusher and/or plunger; an actuator that includes a lever pivotally coupled to syringe actuation apparatus to actuate a drive or drive assembly; a syringe having a barrel and a lever having a distal end adjacent to and radially spaced from the distal end portion of the barrel; a lever having a distal end and a syringe having a barrel and a needle where the lever is in non-overlapping relation with the needle (e.g., throughout its full stroke); a stop member coupled to the syringe actuation apparatus and having a contact portion at a preset location to limit advancement of the lever to dispense a predetermined (or desired or preset) amount (or of volume) of substance from the syringe; a stop member coupled to the syringe actuation apparatus and having a contact portion with an adjustable position to provide variable preset stops to advancement of the lever so that a predetermined (or desired or preset) amount (or volume) of substance to be dispensed from the syringe can be varied; the position of the travel limit device is adjustable to adjust the lever travel such that multiple and variable predetermined (or desired or preset) amounts (or volumes) of substance can be dispensed from the syringe; an actuator configured to deliver a plurality of predetermined (or desired or preset) amounts (or volumes) of substance from a syringe or to deliver different predetermined (or desired or preset) amounts (or volume) of substance from a syringe; syringe actuation apparatus with a syringe mounted thereto configured so that they can be held in one hand of a user and operated or used only with that hand; a syringe containing a pharmaceutical product used in the treatment of facial lines and/or wrinkles; a reusable syringe actuation apparatus; a syringe actuation apparatus with multiple syringe supports to which the syringe is mounted or secured; a syringe actuation apparatus with a surface (e.g., a curved shaped surface) to which the syringe is mounted or secured; or actuation apparatus which a syringe is releasably mounted.

Further, a dose or a dosage can be an amount of substance.

The above is a brief description of some deficiencies in the prior art and advantages of the present invention. Other features, advantages, and embodiments of the invention will be apparent to those skilled in the art from the following description and accompanying drawings, wherein, for purposes of illustration only, specific forms of the invention are set forth in detail. Variations of the access device and procedures described herein include combinations of features of the various embodiments or combination of the embodiments themselves wherever possible.

BRIEF DESCRIPTION OF DRAWINGS

FIG. 7A is a diagrammatic partial sectional view taken generally along line 7A-7A in FIG. 2.

FIG. 7B is a top diagrammatic view of the housing illustrated in FIG. 7A showing the housing sidewall edges that are secured to the syringe actuation apparatus frame or base.

FIG. 7C is a top diagrammatic view of the stop device or assembly for the lever arm depicted, for example, in FIG. 1.

FIG. 7D is a diagrammatic enlarged partial sectional view of the release mechanism generally diagrammatically depicted in FIG. 7A.

FIG. 7E diagrammatically illustrates the push button and lever arm of 7D rotated 180 degrees.

FIG. 7F diagrammatically illustrates a transverse cross-sectional view taken generally along line 7F-7F in FIG. 7D.

FIGS. 11A and 11B show respective front and rear views of the device 100 of FIG. 10.

FIG. 13 shows a bottom view of the variation shown in FIG. 10.

DETAILED DESCRIPTION

Figure 1:
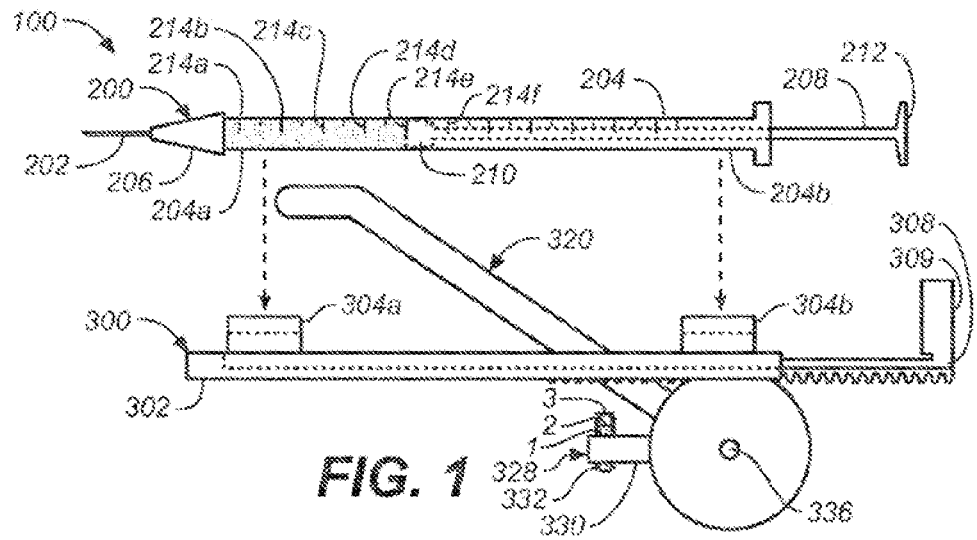
FIG. 1 is an exploded diagrammatic view of a handheld dispensing system (or apparatus) according to one embodiment of the invention.

Before the present invention is described, it is to be understood that this invention is not intended to be limited to particular embodiments or examples described, as such may, of course, vary. Further, when referring to the drawings like numerals indicate like elements.

According to one embodiment of the invention, a handheld medicinal or medical substance delivery system (or apparatus) comprises actuation apparatus, which can be a mechanical actuation apparatus, and a medicinal or medical dispenser (e.g., syringe) where the dispenser is mounted or coupled to the actuation apparatus such that one can manually manipulate the actuation apparatus to deliver a substance (e.g., any suitable pharmaceutical product or agent used in the treatment of facial lines and wrinkles such as a paralytic agent) from the dispenser to a patient site or target site (e.g., muscle layer immediately beneath the skin) or to each of a plurality of patient sites or target sites, while holding the substance delivery system. The actuation apparatus can be configured to provide the operator flexibility in an amount of substance to be delivered by, for example, allowing the operator to determine the extent the actuation apparatus is actuated. For example, the operator need not fully actuate the actuation apparatus so that a smaller amount or volume of substance is dispensed. The actuation apparatus also can be configured to allow the operator to deliver a desired, preset or predetermined amount or volume of the substance. It also can be configured to facilitate repeatable delivery of the same desired, preset or predetermined amount or volume of substance, which can facilitate delivery of reproducible precise amounts or volumes of substance from the dispenser. A precise amount can, for example, correspond to a drop of liquid, where the size of the drop can depend on the density of the liquid and the surrounding pressure, or a value such as 0.1 cc of substance. In contrast, delivery of precise reproducible amounts or volumes of substance may be difficult if possible with a traditional method of holding a syringe in one hand and depressing the plunger with the other hand or the thumb of the same hand.

Further, the actuation apparatus described in the preceding paragraph can be provided with an optional adjustment mechanism to facilitate delivery of different desired, preset or predetermined amounts (or volumes) of substance or different doses or dosages.

The substance delivery system also can be configured to be held and used with a single hand (e.g., in a manner that resembles holding a pen), which can enhance controllability and stability of the system during use. Further one handed operation of the system enables its user (e.g., operator or physician) to use his/her free hand to do something else. For example, when using the system to treat wrinkles, one handed operation allows the user's free hand to hold the patient's skin and stretch the skin in the areas of wrinkles, which facilitates the proper placement of the delivered agent with the other hand. Thus, with this configuration, a single hand can be used (or only one hand is needed) to hold the agent or substance delivery system, maneuver it to the desired site, direct it to penetrate the syringe needle at the desired site, and manipulate the syringe actuation apparatus to inject a desired amount of the agent or substance into the patient. In one embodiment according to the invention that facilitates such use, actuation apparatus includes a lever actuator having one end adjacent to or radially spaced from a distal portion or the distal end of the syringe barrel and its other end coupled to the actuation apparatus. This can enhance one handed control of the device. For example, a bottom portion of the delivery system can be held in the web space of the hand between the index finger and thumb and the user's index finger used to depress the lever actuator. The lever actuator end that is adjacent to the distal portion or end of the syringe barrel can be in non-overlapping relation to the exposed portion of the needle so as not to interfere with inserting the needle into the patient. Further, the lever can be pivotally mounted to the apparatus such that the user can squeeze the lever with one hand, while holding the system with that hand to dispense substance from the dispenser. With this lever configuration the user may be able to sense back pressure and control delivery rate of the substance being dispensed. Since the lever arrangement can enhance one's ability to use the device with a single hand, it can improve its ease of use. Further, the one-handed aspect can enhance stability of the system during use.

The syringe actuation apparatus also can be configured so as to be reusable. For example, it can be configured so that the dispenser or syringe is releasably or removably mounted or coupled thereto so that, for example, a used dispenser or syringe can be replaced with a new dispenser or syringe. Further, the actuation apparatus can be configured to be coupled to an off-the-shelf medical dispenser or syringe.

According to one embodiment of the invention, a handheld medicinal or medical substance dispensing system comprises a syringe (or dispenser), which can have a barrel containing a medicinal or medical substance, releasably or removably mounted or coupled to the base or frame of actuation apparatus. The actuation apparatus includes a pusher (or slide) slidably mounted to the base or frame of the actuation apparatus and a lever that can be displaced to actuate or move the pusher. The lever can be arranged with an end located adjacent to a distal end or end portion of the syringe barrel, which can be fitted with a needle. The system can include a mechanism (e.g., a stop positioned at a preset location to limit the maximum displacement of the lever from a start position) such that when the lever is fully displaced from the start position, the lever actuates the pusher (or slide) to move the syringe plunger in the syringe barrel a specific distance, which is reproducible (e.g., when the lever is again fully displaced from its start position). In one variation, the specific distance that syringe plunger travels, which can be the same distance that the pusher travels, can be adjusted, and the adjusted distance reproducible using, for example, an adjustable mechanism to preset the adjusted maximum lever displacement. For example, the pusher and syringe plunger travel distance can be preset using an adjustable stop that provides an adjustable limit on the maximum displacement of the lever from its start position so that the preset plunger distance and dispensed substance can be varied.

This specific syringe plunger travel distance, which can be preset based on, for example, the position of the lever stop, can translate into a known and again, reproducible volume of substance or material being discharged from the syringe as described above, which can enable the user to repeatedly deliver a desired, preset or predetermined amount of substance (e.g., a fluid or paralytic agent) to, for example, the face of a patient to treat facial lines or wrinkles. The system also may be used to repeatedly deliver a dosage of the substance described above to treat facial lines or wrinkles. The dosages can be varied as well. In general, the lever, pusher, and plunger travel amount(s) or distance(s), movement amount(s), or displacement(s) can be preset e.g., through a lever stop, to dispense, deliver, eject, or inject a desired, preset or predetermined amount(s), volume(s), dose(s) or dosage(s) of substance. For example, the maximum lever displacement can be preset so that the pusher and/or plunger move a desired, preset or predetermined distance to dispense a desired, preset or predetermined amount of substance from the syringe.

Further, the system can be configured so that it can be supported by one hand, which can enhance its stability during use and the lever arrangement can enhance one's ability to use the device with a single hand and improve its ease of use.

Figure 2:
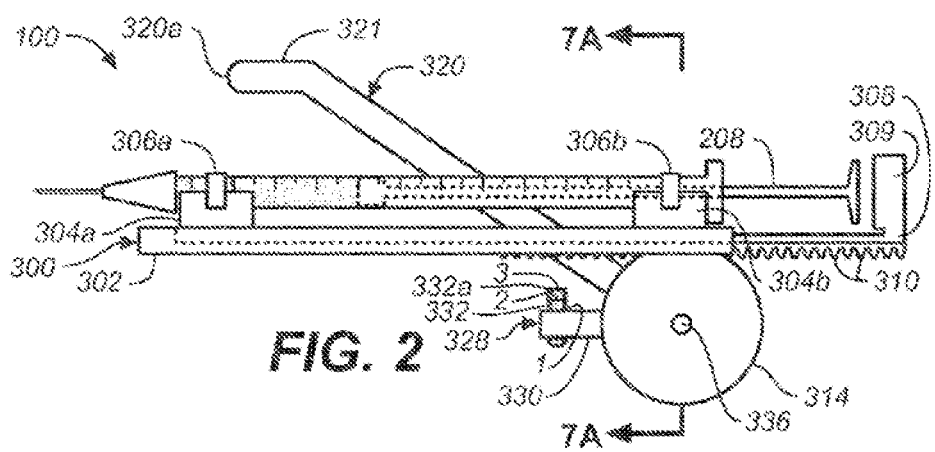
FIG. 2 diagrammatically illustrates a side elevational view of the embodiment of FIG. 1 assembled with the syringe mounted on the system's syringe actuation apparatus of FIG. 1 and the actuation apparatus pusher member spaced from the syringe plunger.

Referring to FIGS. 1 and 2, an illustrative example of one embodiment of the invention is shown. FIG. 1 is an exploded view of handheld medical substance dispensing, delivery, ejecting or injecting system 100, which includes syringe 200 and syringe actuation and/or metering apparatus or device 300. FIG. 2 shows syringe 200 releasably or removably coupled or mounted to syringe actuation apparatus 300.

Syringe 200, which can be any standard hypodermic syringe having a hypodermic needle 202 to inject fluid (e.g., a liquid or gas) into body tissue, a barrel or tube 204 to which the needle is coupled, and a plunger 208 slidably moveable in barrel 204.

Returning to FIG. 1, barrel or tube 204 has a distal end portion 204a and a proximal end portion 204b, holds fluid (e.g., any known suitable paralytic agent or dermal tiller to treat facial lines or wrinkles), and has an orifice at one end for the fluid to be dispensed therefrom into needle 202. Plunger 208 has a piston head 210 that fits snugly in barrel 204, and thumb actuator or handle 212 that can be pushed to dispense fluid from the barrel and needle. The barrel can be provided with a distal tapered tip 206 to which the needle is attached or fined and it can be transparent so that the amount of fluid or substance therein can be monitored. Syringe barrel 204 can have graduated marks or indicia 214a, b, e, d, e, f . . . n to indicate the volume of fluid therein. In the illustrative example, the volume between any adjacent two of these lines (e.g., 214d and 214e) corresponds to 0.1 cc. The marks between these lines further indicate 0.05 cc quantities. Any suitable material can be used to make the barrel such as plastic or glass.

Although one syringe configuration is shown, any suitable syringe configuration can be used as would be apparent to one of ordinary skill in the art. For example, a syringe without a needle, but to which a needle can be fitted, e.g., a disposable needle, can be used.

Before mounting the syringe to the base, the operator or physician can perform an air removal procedure as is known in the art and tap the syringe while holding it with the needle up and then pushing the syringe plunger to dispense some liquid. Alternatively, the operator or physician can use syringe actuation apparatus 300 to remove air from the syringe as will be described in more detail below.

Syringe 200 is releasably or removably coupled or mounted to syringe actuation or metering apparatus or device 300. In the illustrative example, syringe actuation apparatus 300 includes a base or frame 302 to which syringe supports 304 are attached. Alternatively, the frame and supports, which can be any suitable material such as plastic, can be integrally formed as a single piece construction. As shown in FIG. 7A, support 304b has a curved surface (which can, for example, be a concave or U-shaped surface) in which syringe barrel 204 is cradled. Support 304a, which is hidden from view in FIG. 7A, has the same configuration. Although one curved surface is shown formed in support 304b any other suitable surface for supporting the syringe can be used.

Syringe 200 can be secured to syringe actuation apparatus base 302 using any suitable means. In the illustrative example, straps 306a,b secure syringe barrel 204 to supports 304a,b (see e.g., FIGS. 2 & 7A). Since each strap is secured to a respective support in the same manner only securement of strap 306b will be described for simplification. Strap 306b has a first end 306b1 fixedly secured to a support 304b (e.g., along a support side) and a second end 306b2 that is detachably secured to support 304b (e.g., the other side of the support) so that the strap extends over the syringe barrel and snugly holds it against the support so as to preclude or minimize relative axial movement therebetween. Any suitable detachable securing mechanism can be used to detachably secure the second end 306b2 to the support. For example, hook and loop fasteners, which can be Velcro® brand hook and loop fasteners, can be used. A band of hook fasteners can be provided along one side of a strap to engage with a band of loops provided along a portion of the support. Alternatively, a band of loop fasteners can be provided along one side of a strap to engage with a band of hooks provided along a portion of the support. In one variation, both strap ends can be detachably secured to their respective support. It also should be understood that although two supports are shown, one support, two supports, more than two supports, or no supports can be used. For example, a curved surface can be formed in base 302 or no curved surface provided in which case a securing mechanism is still used to secure syringe 200 to syringe actuation apparatus 300.

Syringe actuation apparatus 300 also includes an actuator that can move syringe plunger 208 toward syringe needle 202 to dispense or inject a plurality of desired volumes or predetermined volumes of substance. In the illustrative example, one such actuator is shown and includes pusher or pusher member 308, lever or lever arm 320, and a drive or drive assembly coupling pusher member 308 and lever arm 320. A mechanism to vary the desired volumes or predetermined volumes of substance to be dispensed also can be included as will be described below with reference to the exemplary embodiment shown in FIG. 1. It should be understood, however, that although one actuator configuration will be described, other actuator configurations that can move syringe plunger 208 in syringe barrel 204 toward syringe needle 202 to dispense or eject a plurality of desired volumes or predetermined volumes of substance can be used as well as other mechanisms to vary the desired volume or predetermined volume of substance to be dispensed or injected into the patient.

Referring to FIGS. 1 and 7A, base 302 has a longitudinal channel or slot 302a formed therein and in which pusher 308 is slidably mounted such that it can move generally parallel to plunger 208 of syringe 200 when the syringe is mounted to base 302 as shown in the drawings. Slot 302a can extend the entire length of base 302 and can have a configuration that cooperates with the configuration of pusher 308 as shown, for example, in FIG. 7A, such that pusher 308 is maintained in the slot and does not fall out from base 302 when oriented, for example, as shown in FIG. 7A. In the illustrative example, slot 302a has a first portion 302a1 adjacent its opening with a first width and a second portion 302a2 inwardly positioned from the first portion with a second width greater than the first width. Pusher 308 has a corresponding first width adjacent its teeth 310 and second width that forms lateral extensions that mate with the wider portion of slot 302a as shown in FIG. 7A. Although one slot-pusher configuration has been shown, it should be understood that other configurations or mechanisms can be used to maintain pusher 308 in the slot formed in base 302. For example, when ratchet wheel housing 314 is secured to base 302 and secures ratchet wheel 316 in engagement with pusher teeth 310 as will be described below, ratchet wheel 316 can maintain pusher 308 in the slot formed in base 302 in which case pusher can have a single width. However, a slot configuration as described above can be helpful in assembly of the apparatus and avoid the need for the ratchet wheel to hold up the pusher. Housing 314 also can comprise separate components that are assembled around the mechanisms to be mounted therein as would be apparent to one of ordinary skill in the art. It also should be understood that housing 314 may have other configurations than the circular one shown. For example, housing 314 can be square or rectangular with one side open for attachment to base 302.

Figure 3:
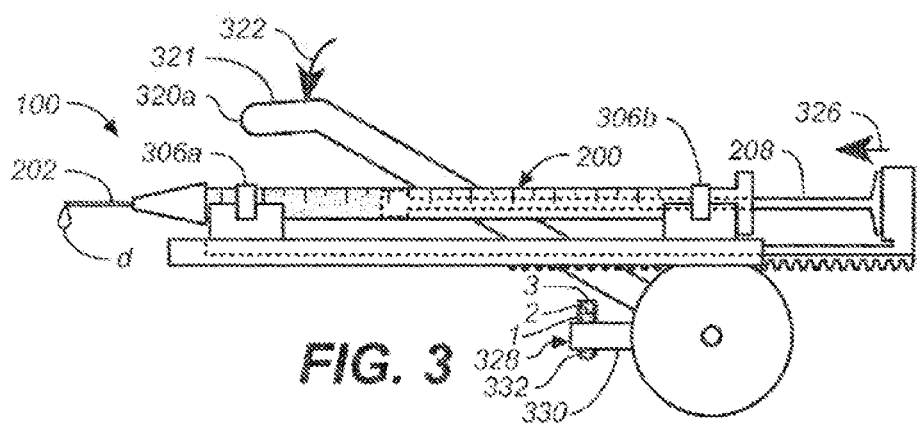
FIG. 3 diagrammatically illustrates the system of FIG. 2 with the illustrated lever arm partially depressed to have the pusher member engage the syringe plunger thumb portion and advance the syringe plunger so as to eject a small amount of fluid form the syringe needle to prepare the apparatus for use.

Pusher teeth 310 extend from the bottom of pusher 308 and along its length to cooperate with driving gear teeth 318 of ratchet wheel 316 so that ratchet wheel 316 can move or drive pusher 308 toward plunger handle or plunger thumb actuator portion 212 of syringe plunger 208 or move pusher 308 and plunger portion 212 therewith when pusher 308 and plunger portion 212 are in engagement as shown in FIG. 3. Pusher 308 includes a portion or extension 309 that extends in a direction opposite from pusher teeth 310 and is arranged or aligned to engage and press against plunger handle or plunger thumb portion 212 of syringe plunger 208. In this manner, pusher portion 309 advances the plunger in syringe barrel 204 when pusher 308 is moved toward the distal or needle end of syringe 200. For example, in FIG. 4, apparatus 300 is in a state where pusher 308 is not advancing plunger 208 as system 100 is moved toward a patient treatment site as shown with direction arrow 102a. Needle 202 is then penetrated though the skin "S" of a patient at treatment site as shown in FIG. 5, after which lever 320 is fully depressed in the direction of arrow 322 rotating ratchet wheel 316 in the direction of arrow 324 to advance pusher 308 and plunger 208 therewith in the direction of arrow 326 (FIG. 5) to inject medicinal substance into the patient. After the injection, system 100 can be retracted or removed from the patient as indicated with direction arrow 102b (FIG. 6) without moving the ratchet wheel or plunger. This can be repeated at one or more different sites to deliver a desired amount or predetermined amount of substance to the patient at each site.

Any suitable known ratchet assembly can be used as part of the drive to rotate the drive in one direction such as a ratchet assembly having a ratchet wheel having inner ratchet teeth and outer gear teeth combined with spring loaded pawls.

Figure 8A:
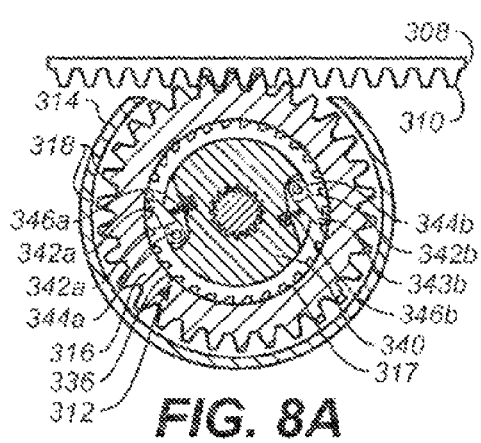
FIG. 8A diagrammatically illustrates a ratchet mechanism, generally shown in FIG. 7A, for advancing the pusher member.
Figure 8B:
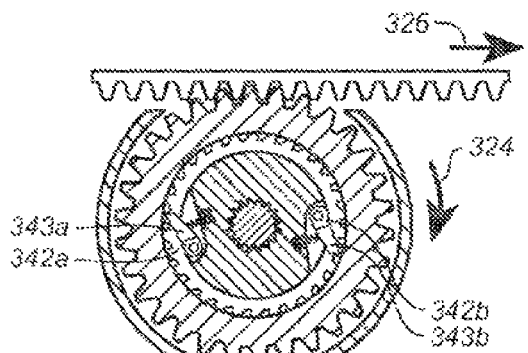
FIG. 8B diagrammatically illustrates the mechanism of FIG. 8A with the ratchet wheel of FIG. 8A rotated and the pusher member advanced.

Referring to FIGS. 7A and 8A-B, one drive or drive assembly using a ratchet mechanism is shown in the illustrative embodiment for purposes of example. In this example, lever arm 320 is coupled to pusher 308 through a drive or drive assembly. The illustrated drive or drive assembly includes ratchet mechanism 312 (see e.g., FIG. 8A), which generally comprises ratchet wheel 316, which also serves as a driving gear wheel, and pawls 342a,b as will be described in more detail below. In brief lever 320 turns or actuates ratchet wheel 316 to drive pusher 308 toward the distal end of syringe 200.

Ratchet mechanism 312, which is housed in ratchet housing 314 (see e.g., FIG. 8A) with axle or pin 336 extending therefrom to lever arm 320 (FIG. 7A), includes ratchet wheel 316 with inner ratchet teeth 317 extending along an inner annular surface thereof. Ratchet wheel 316 also has outer gear teeth 318, which cooperate with pusher teeth 310 to drive pusher 308 in the direction indicated with arrow 326 as shown in FIG. 8B and in this manner forms a circular gear. Inner ratchet teeth 317 cooperate with ratchet pawls 342a,b, which are pivotally coupled to or are supported on pawl support 340, which is fixedly secured to pin or axle 336, which extends through a center hole formed in pawl support 340. Ratchet pawls 342a,b are pivotally mounted to pawl support or wheel 340 on pins 344a,b (see e.g., FIG. 8A), which are secured to pawl support 304 and spring loaded with springs such that they are biased or urged toward inner teeth 317 to allow ratchet wheel 316 to rotate in only one direction (see e.g., arrow 324 FIG. 8B). In the illustrative embodiment, coil springs 346a,b are placed in recesses in support 340 and arranged to bias or urge the pawls toward inner teeth 317. It should be understood, however, that other spring arrangements or configurations can be used including ones without a recess or ones using other types of springs as would be apparent to one of ordinary skill in the art. Further, pawls 342a,b are made to include ramp or wedge portions 343a,b to assist in releasing the pawls from the ratchet wheel as will be described in more detail below. In operation, when lever 320, which is fixedly secured to pin or axle 336, is depressed, it moves in the direction indicated with numeral 322 in FIG. 5 to actuate the drive assembly. That is, lever 320 rotates pin or axle 336, which is fixedly secured to and rotates pawl support 340, which rotates pawls 342a,b therewith. As pawls 342a,b move with rotating pawl support 340, they push the ratchet teeth 317 with which they are engaged and biased against to rotate ratchet wheel 316 in the direction indicated with arrow 324 as shown in FIG. 8B. As ratchet wheel 316 rotates in this direction with its teeth 318 mating with pusher teeth 310, it drives or moves pusher 308 in the direction of arrow 326 so that pusher extension or arm 309 can engage and advance syringe plunger 208 to dispense fluid. When lever 320 is allowed to return to its start or rest position as shown, for example, in FIG. 6 (e.g., by releasing lever arm 320), lever arm spring 334, which can be a coil spring, moves toward its rest position and lifts or moves lever arm 320 in the direction indicated with arrow 327 (FIG. 6) to its start or rest position. In the example shown in FIGS. 1-7A, spring 334, which urges lever 320 toward its start or rest position, has one end 334a secured to post 335, which extends from base 302, and its other end 334b secured to lever arm 320. In this manner, spring 335 can maintain lever arm in its start or rest position when the lever arm is not being depressed. Other mechanisms also can be used to urge lever arm 320 toward its start or rest position as would be apparent to those skilled in the art.

Figure 8C:
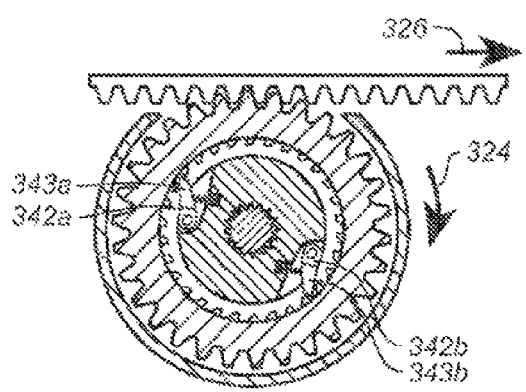
FIG. 8C diagrammatically illustrates the mechanism of FIG. 8B with the ratchet wheel of FIG. 8A further rotated and the pusher member further advanced.

As lever arm 320 returns to its start or rest position, it rotates pawl support 340 through pin or axle 336 in the opposite direction. As pawl support 340 rotates in that opposite direction, pawls 342a,b slide over consecutive ratchet wheel teeth 317, which in the illustrative example, are shown with an asymmetrical configuration where each tooth has a steeper slope on one side as compared to the other. It should be understood, however, that other ratchet teeth configurations can be used as well. Lever arm 320 can again be actuated to further advance ratchet wheel 316 and pusher 308 and this repeated as desired as diagrammatically shown in FIG. 8C.

Although one drive or drive assembly has been shown, it should be understood that many other drives or drive assemblies can be used as would be apparent to one of ordinary skill in the art and that the illustrative example is not intended to limit the scope of the invention.

Figure 8D:
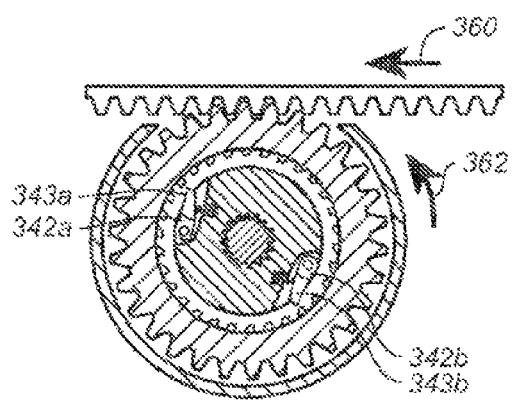
FIG. 8D diagrammatically illustrates the mechanism of FIG. 8C with the pawls moved inwardly and the pusher member being reset or retracted.

Referring to FIG. 8D, release of Pawls 342a,b to reset pusher 308 is shown. When the pawls are moved radially inward as shown and as will be described in detail below, the user can push pusher 308 back as generally indicated with arrow 360 turning released ratchet wheel in the direction indicated with arrow 362. In this manner, the user can reset pusher 308 to a desired position (e.g., back to its position shown in FIG. 2 to ready apparatus 300 for another syringe loaded with the desired agent or substance after syringe 200 has been removed).

Regarding the coupling of lever arm 320 to ratchet wheel 316, lever arm end 320b is fixedly secured to axle 336 or in a recess formed in axle 336 using any suitable means and pin or axle 336 is fixedly secured to pawl support or wheel 340 using any suitable means (see e.g., FIGS. 7A and 7E). For example, glue, adhesive or welding can be used to secure lever arm 320 to pin or axle 336 and a splined connection can be provided between pin or axle 336 and pawl support or wheel 340. Alternatively, all of those connections can be made with for example, glue, adhesive or welding. In this manner, lever arm 320, which is biased toward its rest or start position (see e.g., FIG. 4), can be depressed to move in the direction of arrow 322 (FIG. 5) to rotate pin 336 and pawl support wheel 340 and then released so that it moves as indicated with arrow 327 (FIG. 6) and returns to its start or rest position shown in (see e.g., FIGS. 4 and 6).

Returning to FIG. 7A, pin or axle 336 extends through openings in sidewall 314a,b of ratchet housing 314. Sidewall 314a can be provided with a bearing or bushing 338 to facilitate or enhance rotation of pin or axle 336 therein. Alternatively, the materials used to make the axle and sidewalls of the housing can be selected to facilitate the desired rotation of axle 336 in sidewall 314a without a bearing or bushing. Push button 354, which will be discussed in more detail below, extends through sidewall 314b and provides a support in which pin or axle 336 can rotate. Again the materials can be selected to facilitate the desired rotation as would be apparent to one of ordinary skill in the art.

Referring to FIG. 7B, ratchet housing 314 has a cutaway portion that exposes sidewall edges 315a,b so that they can be fixedly secured to base 302 as shown in FIG. 7A.

Since ratchet wheel 316 is supported by pawls 342a,b, which are mounted on pawl support 340, which is mounted on pin 336, which is mounted in housing 314, which is secured to base 302, ratchet wheel 316 is supported in housing 314 in engagement with pusher teeth 310. Alternatively, a ratchet wheel holding mechanism can be used to maintain the ratchet wheel in the desired position as shown in FIG. 7A. In this arrangement, ratchet wheel holding mechanism 319 comprises a disk 319a having an outer portion 319a1 fixedly secured to ratchet wheel 316, an inner portion 319a2 aligned with pawl wheel 340 and not secured thereto so as to allow relative movement between inner portion 319a2 and pawl wheel 340, and cylindrical hub 319b that is rotatably mounted on axle 336 and from which disk inner portion 319a2 extends. Inner portion 319a2 also is rotatably mounted to axle 336, which extends through a central opening in inner portion 319a2. Inner portion 319a2 also can be recessed so as to be spaced from pawl wheel 340. Further, holding mechanism 319 can be formed as a single unitary element and can comprise any suitable material such as plastic.

As discussed above, lever arm 320 can be configured and/or arranged to facilitate one handed use of the system. In the illustrative embodiment, lever arm 320 has a distal end or free end 320a (FIGS. 1-6), a proximal end 320b (FIG. 7E), and a portion 321 (FIGS. 1-6), which can be used to push, actuate or depress lever arm 320 in the direction of arrow 322 (see e.g., FIG. 5). Portion 321 can be angled to extend generally parallel to the longitudinal axis of syringe barrel 204 or syringe needle 202 when the syringe is mounted to syringe actuating apparatus 300. The position of portion 321 adjacent to the distal end portion of syringe barrel 204 and its depicted configuration can enhance the ease in which a finger can depress lever 320. However, other configurations can be used. Lever arm distal end or free end 320a is arranged to move alongside barrel 204. It also is adjacent to the distal end portion of syringe barrel 204 and in non-overlapping relation with needle 202 so as not to interfere with placement of the needle in the patient as shown, for example, in FIGS. 4 and 5 where the lever arm is shown in non-overlapping relation with needle 202 throughout a full stroke. Lever free end 320a or the distal free end portion of lever 320 also can be radially spaced from barrel 204 as shown in FIG. 7A.

In the embodiment shown in FIGS. 1-6, a mechanism is provided so that the dispensing system can deliver a desired, preset or predetermined amount or volume of substance. In one embodiment, a mechanism is provided to limit the movement or advancement of lever arm 320 (or limit the maximum arc or arc length that it can travel) in the direction of arrow 322 (see e.g., FIG. 5). In this manner, the limiting mechanism also limits the corresponding rotation of ratchet wheel 316 and translation of pusher 308. This limiting mechanism is arranged so that the travel distance or displacement of lever arm 320, ratchet wheel 316, and/or pusher 308, upon full depression or actuation of lever arm 320 from its start position, can be preset in a manner such that a plurality of desired, preset or predetermined volumes of substance can be dispensed or ejected from syringe 200. The maximum movement of lever arm 320 can be preset to drive to ratchet wheel 316 and/or pusher a preset distance. In the illustrated embodiment, a lever stop or lever travel limit device (e.g. stop or limit device 328) is provided. Stop 328 has an arm 330 that extends from ratchet housing 314 and turns 90 degrees or any suitable amount so as to extend into the path of lever arm 320. Arm 330 has a first portion 330a that extends from housing 314 and a second portion 330b that extends into the path of lever arm 320 (see e.g., FIG. 7C). The stop sets or defines the fully advanced position of lever 320 as lever 320 cannot travel beyond the stop. In another embodiment, the stop can be formed with a member that extends from base 302 and under lever 320. When the stop does not have an adjustable stop member, syringe actuation apparatus 300 can be calibrated with syringe 200 or any syringe or dispenser to be used therewith using known techniques to locate where the stop will be located or preset to provide a desired, preset or predetermined amount or volume of substance to be ejected.

Referring to FIG. 1-6, stop arm 330 of stop 328 can include an optional mechanism or member to vary the maximum displacement of lever arm 320 or the maximum stroke or maximum distance or arc that lever arm 320 travels to vary the desired, preset or predetermined amount or volume to be dispensed. In the illustrative embodiment, stop arm 330 can be provided with an optional threaded bore in which an optional stop member or set screw 332 is rotatably positioned so that set screw 332 can be raised or lowered to change or adjust the range of movement that lever arm 320 can travel. Set screw 332 has a contact surface or portion 332a that lever arm 320 contacts upon full advancement thereof where the contact portion position is adjustable since set screw 332 can be raised or lowered such that the desired, preset or predetermined amount of substance to be dispensed from the syringe can be varied. Set screw 332 can include any suitable means for assisting in rotating it to move it up or down such as a slot in its lower end or any other suitable mechanism as would be apparent to one of ordinary skill in the art.

Set screw 332 can include indicia to indicate a desired, preset or predetermined dispensing, ejecting, or injection amount or volume so that it can be positioned at a desired location or preset to provide a desired, preset or predetermined amount or volume of dispensed substance. For example, the indicia can permit the user (e.g., operator or physician) to adjust set screw 332 (the stop member), so that the amount or volume of dispensed substance can be varied (e.g., to eject 0.1 cc, 0.2 cc, or 0.3 cc from the syringe). These volumes can, for example, correspond to desired, preset or predetermined amounts or volumes of substance to be dispensed. Syringe actuation apparatus 300 can be calibrated with syringe 200 or any syringe or dispenser to be used therewith using known techniques to create the indicia and provide this result. For example, marker lines "1," "2", and "3" can be created by calibrating actuation apparatus 300 with syringe 200 so that 0.1 cc, 0.2 cc, or 0.3 cc are ejected from the syringe upon full displacement of lever arm 320 when set screw 332 is at certain levels and providing the marker lines on the set screw based on the results.

Figure 4:
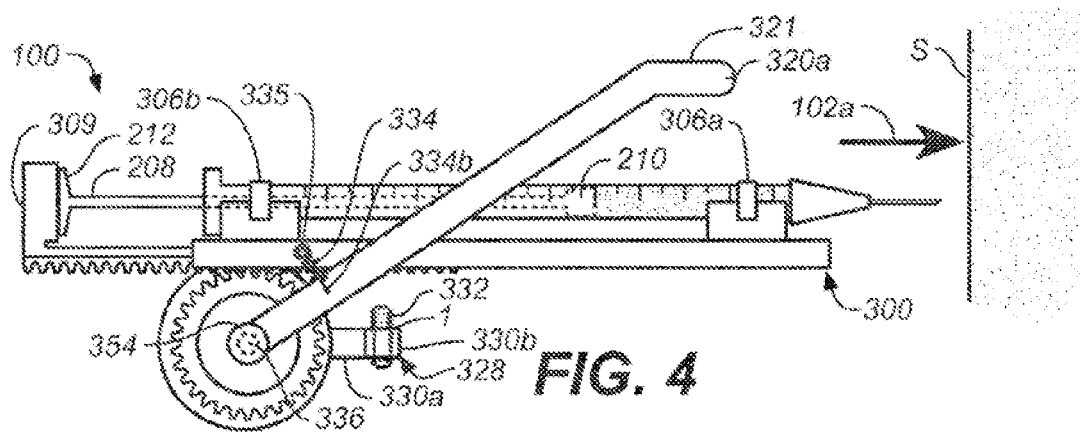
FIG. 4 diagrammatically illustrates the system of FIG. 3 from the opposite side and after the lever arm has been released and allowed to return to its start or rest position as shown in FIG. 2 and being advanced toward a target site on the skin of the patient.
Figure 5:
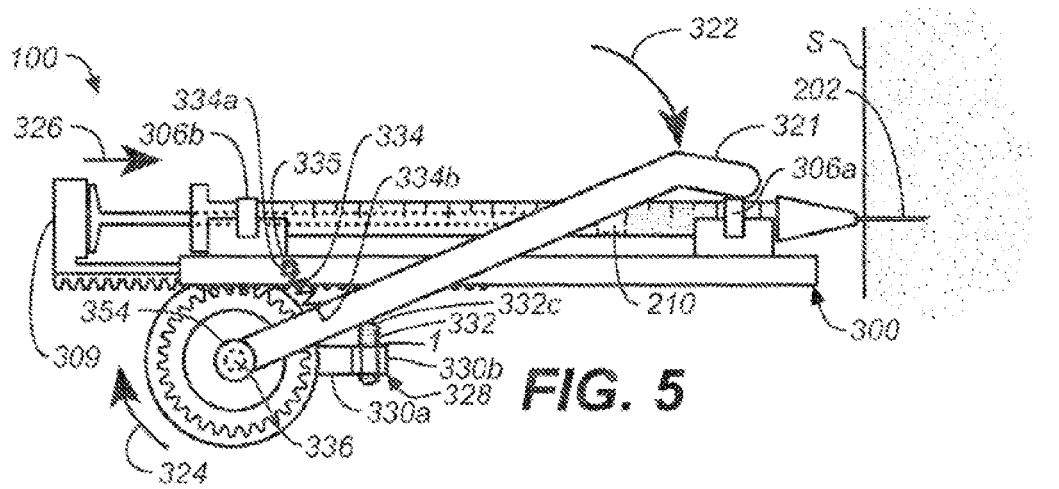
FIG. 5 diagrammatically illustrates the system of FIG. 4 after an operator or physician has penetrated the patient's skin with the needle and fully depressed the lever arm to engage the lever stop member to dispense a desired volume or a preset and/or predetermined volume of substance from the syringe.

Thus, and with reference to, for example, FIGS. 2, 4 and 5, system 100 can be calibrated so that the position of stop member or set screw 332 can be preset as shown, for example, in FIG. 2 or 4 so that the pusher moves the plunger a desired, preset, or predetermined distance (the pusher can move the same distance to provide this result) to provide a desired, preset or predetermined ejection or 0.1 cc of substance (e.g., fluid) from syringe 200 when lever 320 is depressed from its start position as shown, for example, in FIG. 4 to a fully depressed position as shown in FIG. 5 where the lever arm contacts set screw 332. When set screw 332 is in this position, the bottom of marker line "1" is aligned with or flush with the upper surface of stop arm 300 (see e.g. FIG. 4). Referring to FIG. 2, when marker line "2" has been created based on a calibration to provide 0.2 cc of substance (e.g., fluid) and stop member or set screw 332 adjusted or lowered so that the bottom of marker line "2" is aligned or flush with the upper surface of stop arm 330 and lever arm 320 is depressed from its start position to where it contacts stop member or set screw 332, 0.2 cc of substance (e.g., fluid) is dispensed from syringe 200. Another marker line, e.g., marker line "3" (see e.g. FIG. 2), can be provided above marker line 2 such that when its bottom is aligned or flush with the upper surface of stop arm 330, 0.3 cc of substance (e.g., fluid) is dispensed when lever arm 320 is depressed from its start position to where it contacts stop member or set screw 332.

The ability to preset the maximum displacement of lever arm 320, which activates pusher 308 to move plunger 208 in syringe barrel 204 a specific distance, which is adjustable and can be preset based on, for example, the position of lever stop member 332, can translate into a known and again, reproducible, volume of substance or material being discharged from the syringe as described above, which can enable the user to repeatedly deliver desired, preset or predetermined amounts or volumes or substance (e.g. a fluid such as a paralytic agent) to a patient. This can, for example, enhance the user or operator's ability to obtain symmetry of results or to deliver the desired agent symmetrically over a region.

It is further noted that the (1) lever arm actuator or (2) lever arm stop or stop member taken individually or in combination contribute to the ergonomics of the handheld dispensing system.

Regarding the pawl release described above, one example of a pawl release mechanism for releasing the pawls to reset pusher 308 is diagrammatically shown, for example, in FIGS. 7D-F and generally designated with reference numeral 350. Referring to FIG. 7D, release mechanism 350 generally comprises push button 354, open cylinder 351, which the push button moves to cooperate with pawl ramp or wedge portions 343a,b of pawls 342a,b, and a biasing mechanism such as coil spring 352 that biases cylinder 351 away from pawls 342a,b.

Push button or actuator 354 is a hollow tubular member having a closed end 354a and an open end 354b. Push button 354 is rotatably and slidably mounted on axle 336 and has a slot or window 356 formed therein through which lever arm 320 extends as diagrammatically depicted in FIG. 7E, which diagrammatically illustrates the push button and lever arm of FIG. 7D from the opposite side. The cut-out in push button 354 that forms slot 356 has an upper edge 356a, a lower edge 356b, and side edges 356c,d. FIG. 7F diagrammatically shows a transverse section view of the push button and lever arm of FIG. 7E and the slot upper edge 356a and lower edge 356b. The width "w" of slot 356 is sized so that lever arm 320 can travel its intended or desired distance or stroke when depressed or released. Length "l" of slot 356 is sized to permit operation and sliding of push button 354 about lever arm 320 so that the push button can be pushed to release the pawls and allowed to return to its unactuated position.

Push button 354 also extends over axle 336 through an opening in ratchet housing sidewall 314b as shown, for example, in FIG. 7D where it engages coil spring 352 and can move back and forth in the sidewall opening. Coil spring 352 surrounds axle 336 and has one end abutting pawl support 340 and its other end abutting the annular edge face at the open end of push button 354. In this manner, coil spring 352 biases or urges push button 354 toward its start position or unactuated position as shown, for example, in FIG. 7D. Open cylinder 351, which can be a shallow cylinder as shown, comprises a cylindrical wall 351a with an open end and annular wall portion 351b at its other end. Annular wall portion 351b has a center opening through which push button 354 extends and is fixedly secured as indicated with reference numeral 353. The fixed connection between annular wall portion 351b and push button 354 can be made with any suitable means such as welding, adhesive or glue that is applied, for example, continuously for 360 degrees or less than 360 degrees or is applied non-continuously in a spaced pattern. Spring 352 urges push button 354 away from pawl support 340 and through push button 354 spring 352 urges annular wall portion 351b of cylinder 351 against housing sidewall 314b. In this manner, an operator can push button 354 toward pawl support 340 to move the pawls radially inward and then release push button 354 so that is can return to its unactuated position shown in FIG. 7D and as generally indicated with reference arrow 358. Pawls 342a,b are made to include ramp or wedge portions 343a,b, which form part of pawls 342a,b. Ramp or wedge portions 343a,b are diagrammatically shown in FIG. 7D with a tapered configuration with one side sloping radially inward so that when cylinder 351a engages the ramp or wedge portions, it moves pawls 342a,b radially inward. The illustrated tapered configuration or sloping side that forms a ramp can extend the length of the ramp or wedge portions 343a,b, which can, for example, run a short distance from the distal or free end of a respective pawl along the distal end portion of the pawl, or run from the distal or free end of the pawl close to the pivot pin, or a different distance. However, it should be understood that ramp or wedge portions 343a,b can be angled, configured and/or arranged differently than that shown to cooperate with cylinder 351 such that pawls 342a,b are moved radially inward when cylinder 351 is pushed toward pawl support 340 and against such ramp or wedge portions as would be apparent to one of ordinary skill in the art. Other release mechanisms also can be used.

Referring to FIG. 7D, when the user wants to reset pusher 308, the user pushes push button 354 to move the open end of cylindrical member 351 that faces pawl support 340 toward pawls 342a,b. As the open end of cylindrical wall 351a engages the pawl ramp or wedge portions 343a,b, it pushes ramp portions 343a,b or pawls 342a,b radially inward about their pivot pins as diagrammatically shown in FIG. 8D. In this position, the user can reset the position of pusher 308. It also should be understood that other release mechanisms can be used. After resetting pusher 308, push button 354 can be released to allow the pawls to reengage ratchet wheel 316.

The following example is set forth to illustrate one method of operation of the invention, and is not intended to limit the scope of the invention. For example, the method described hereafter will be disclosed in connection with treating facial wrinkles or lines, but is not intended to be limited to such treatment. More specifically, the following example involves injection of a liquid filler or paralytic agent in a facial line or wrinkle to paralyze selective muscles of the face in order to provide diminishment and smoothing of the line or wrinkle. The injection can be repeated to treat other lines or wrinkles or to add more liquid tiller to a treated line or wrinkle.

Syringe 200, which contains a paralytic agent as described above, can be primed to remove air therefrom before it is mounted to syringe actuating apparatus 300 as described above or syringe actuation apparatus 300 can be used to prepare the syringe for use. In the latter case, syringe 200 can be secured to syringe actuation apparatus 300 and the apparatus held so that syringe needle 202 extends upwardly. Then syringe actuation apparatus 300 can be actuated by pressing lever arm 320 (e.g., with the index finger) to advance pusher portion or arm 309 into contact with the syringe proximal end portion or thumb portion 212 of syringe plunger 208 if not engaged therewith (FIG. 2), and then further actuated by further depressing lever arm 320 to advance syringe plunger 208 in syringe barrel 204 to dispense a first small amount of substance (e.g., a drop of substance "d") to prepare the syringe for use as shown in FIG. 3. FIG. 3 shows lever arm 320 only partially depressed to dispense a small amount of substance.

If apparatus 300 has not been used to prepare the syringe for use (e.g., the syringe was prepared before securing it to syringe actuation apparatus 300) or pusher extension 309 is not engaged with syringe thumb actuator portion 212 (FIG. 2), lever 302 is depressed to engage pusher 308 with thumb actuator portion 212 and then lever 302 is released to allow it to return to its start position or at rest state as shown in FIG. 4.

Figure 9:
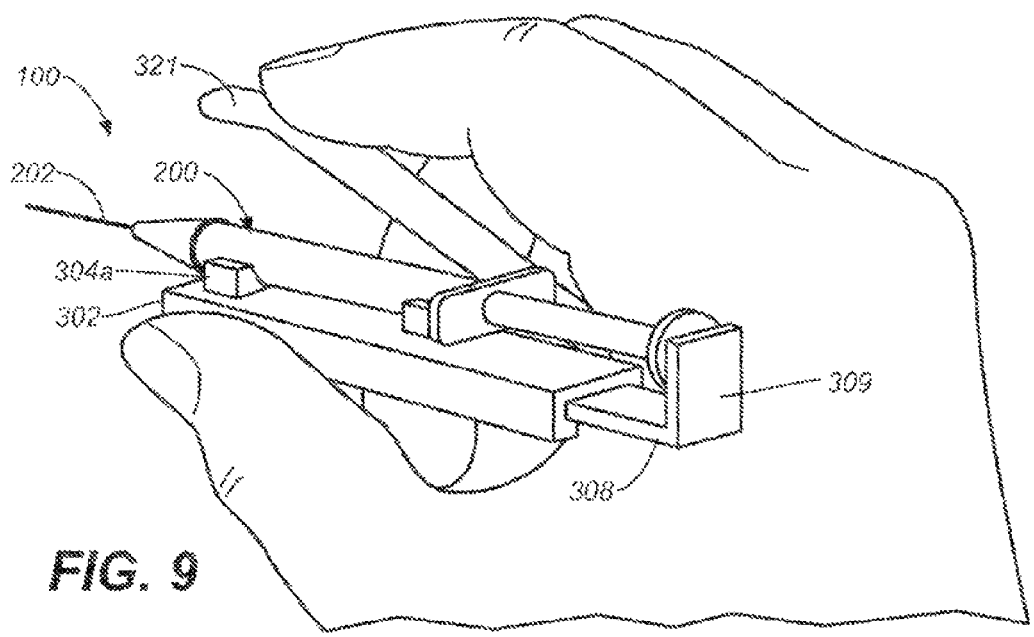
FIG. 9 diagrammatically depicts one method of holding the system of FIG. 2 with a single hand.

With handheld system 100 ready for use, the operator or physician holds system 100 in one hand with the system cradled in the web of the physician or operator's hand between the thumb and index finger and the index finger on lever portion 321 as generally diagrammatically shown in FIG. 9. The middle finger can provide further support for holding the apparatus 300. The operator or physician uses the other hand to hold the patent's skin and stretch the skin in the areas of facial lines or wrinkles to assist in properly placing the syringe needle and delivery of the agent. The operator or physician then advances dispensing apparatus 100 toward a target site on the patient's skin as indicated with arrow 102a in FIG. 4.

Referring to FIG. 5, after the operator or physician has penetrated the patient's skin with syringe needle 202, he or she fully depresses lever arm 320 to engage set screw or stop member 332 of lever stop 328 to move pusher 308 and syringe plunger 208 a desired (or preset and/or predetermined distance) and inject a desired (or preset and/or predetermined) amount (or volume, dose or dosage) of a paralytic agent in the muscle beneath the facial line or wrinkle being treated.

Figure 6:
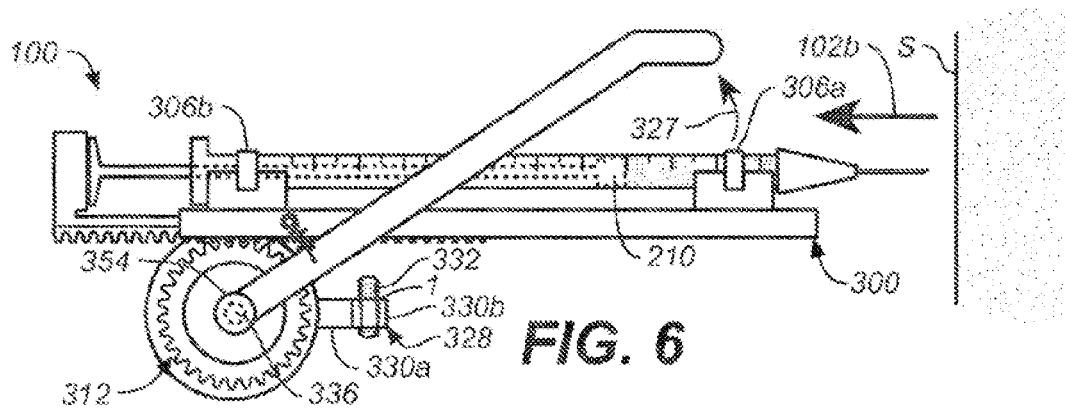
FIG. 6 diagrammatically illustrates the system of FIG. 5 alter the system needle has been removed from the patient and the lever arm released and allowed to return to its start or rest position as shown in FIG. 4.

FIG. 6 shows dispensing apparatus 100 after syringe needle 202 has been withdrawn from the patient and lever arm 320 released and allowed to return to its start position as shown in FIG. 4. The operator or physician can then penetrate the needle into another site to treat other lines or wrinkles or to add more liquid filler to a treated line or wrinkle and this can be repeated until the syringe is emptied or no longer has a desired (or preset and/or predetermined) amount (or volume, dose or dosage) of substance or paralytic agent contained therein. Then syringe 200 can be removed from syringe actuation apparatus 300, pusher 308 reset, and another syringe containing the desired paralytic agent mounted to apparatus 300 to continue treatment of the patient or to treat a different patient. Further, stop member or set screw 332 of stop 328 can be adjusted after any injection to change or vary the desired amount (or volume, dose, or dosage) or the desired (or preset and/or predetermined) amount (or volume, dose, or dosage) of agent to be injected at any point during a procedure.

Figure 10:
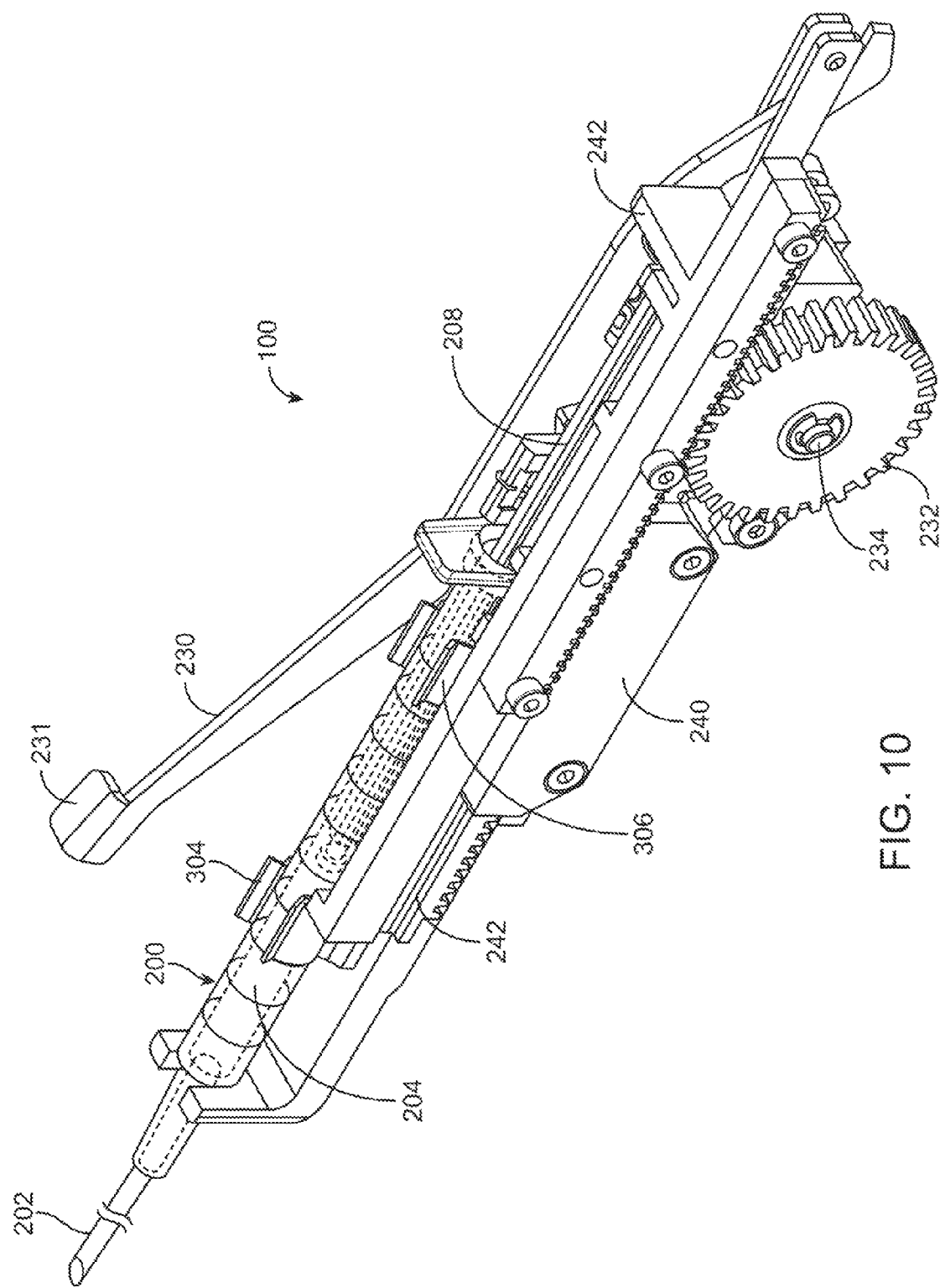
FIG. 10 illustrates an isometric view of a variation of a dispensing unit that is configured to produce a negative pressure within a barrel or reservoir prior to delivering the contents of the substance in the reservoir.

FIG. 10 illustrates another variation of a dispensing unit 100 that is configured to produce a negative pressure within a barrel or reservoir 204 prior to delivering the contents of the substance in the reservoir. The illustrated variation is also shown with the inner mechanism of the device 100 without any outer covering or housing for purposes of clarity. However, any number of coverings, shells, ergonomic fittings, etc. can be provided with the exemplary device shown. As noted below, many variations of the device include coverings that allow a medical caregiver to administer the device using a single hand. Also, additional features can be incorporated into the dispensing unit such as a feedback sensor or other circuitry that can allow for submission of a current through a needle on the syringe or an electrode coupled to the needle and/or syringe.

As shown, the dispensing unit 100 includes a syringe 200 coupled to the device 100. In the illustrated example, the syringe 200 is releasably coupled to the dispensing unit 100 via one or more coupling or securing mechanism 304, 306. Any number of securing mechanisms can be employed in the unit 100. Additionally, alternate variations of the dispensing unit 100 can include a syringe built in or integrated with the dispensing unit.

The device 100 depicted in FIG. 10 includes an actuator 230 that is mechanically coupled to a first gear 232 and a second gear 236 via respective first shaft 234 and second shaft 238 (where in FIG. 10, the second gear and second shaft are located behind a guide member 240). Additional variations of the device 100 permit the caregiver to grasp the device using a thumb and middle finger while using an index finger to operate the actuator 320. Accordingly, the housing (not shown) can be configured to be conducive to such handling. Moreover, in many variations of the device 100 the actuator 320 extends towards a dispensing end (e.g., towards the cannula/needle 202 end of the device). This configuration provides the user the ability to grasp the body or device with an index and middle finger and actuate the lever 230 with an index finger. Clearly, other holding configurations are within the scope of alternate variations of the device of the present disclosure. However, the stability of the device (upon being inserted into tissue) increases when the index finger applies pressure to the lever 230 and the point of contact 231 moves through an arc or path that is close to where the operator is grasping the unit.

FIG. 10 also illustrates a plunger 208 of the syringe 200 being coupled to a plunger fitting 242 that couples the plunger 208 to the lever via the gearing system. Accordingly, the plunger fitting 242 moves the plunger upon activation of the gear drive assembly which is triggered by the actuator 230. As shown, the plunger fitting 242 can also include various keys and channels 242 to allow for smooth advancement of the plunger 208.

The gears in this embodiment are shown as rack-in-pinion gears with the first rack gear 205 moving the plunger 208 in a rearward direction and second rack gear 212 moving the plunger 208 in a forward direction.

FIGS. 11A and 11B show respective front and rear views of the device 100 of FIG. 10. The lever 230 and guide member 240 (not shown) are hidden from view in FIGS. 11A and 11B to better illustrate the drive mechanism of the illustrated variation where the drive mechanism causes movement of the plunger upon movement of the lever actuator 230. As seen in FIG. 11A, a first drive gear 232 engages a first rack gear 250. The first drive gear 232 rotates in response to rotation of a first shaft 232. FIG. 11B illustrates the opposite end of the first shaft 234 being coupled to a drive lever 244. The illustrated variation also includes a back drive gear 238 secured to a back drive shaft 238. The back drive shaft 238 moves upon rotation of a back drive pulley 254.

A variation of the device permits movement of the plunger 208 in a first direction and a subsequent second direction using a single stroke of the lever 230. Typically, this dual directional movement allows a medical caregiver to insert the needle into the patient and then actuate the device 100 such that negative pressure is generated in the reservoir, which causes blood or other fluids to be drawn into the reservoir or a window 203 of the device 100. In certain cases, such as those discussed above, the medical caregiver is attempting to confirm placement of the needle in muscle or other tissue but not in a vessel. If the caregiver determines that the needle is desirably placed via this check stroke, the caregiver can continue to administer the injection using a delivery stroke. One benefit of performing this dual action in a single stroke is that the needle 202 can remain still. This lessens the risk that the needle might inadvertently shift such that the injection is delivered into an undesired area of the body.

FIG. 11B illustrates an example where the stroke of the lever 230 can include one or more segments 110 and 112 to allow for reversing direction of the plunger 208. It is noted that the length of the segments 110 and 112 can be adjusted as desired and that the illustrated segment lengths are for exemplary purposes only.

Figure 12A:
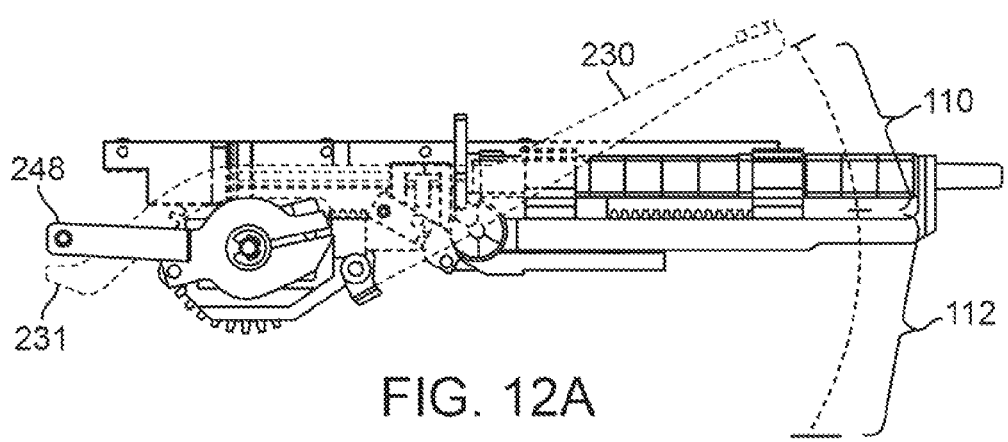
FIGS. 12A to 12E shows an example of the gear drive assembly during movement of the actuator through the first stroke segment.
Figure 12B:
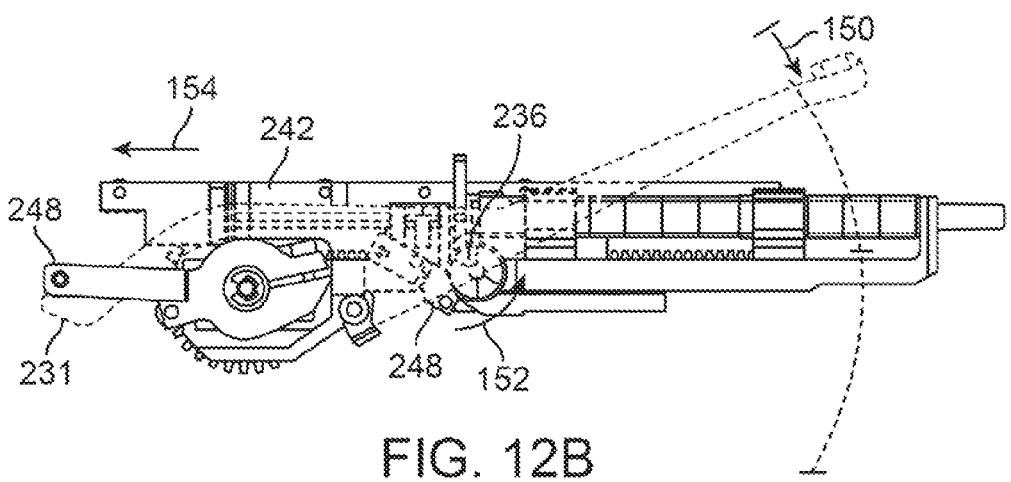
Figure 12C:
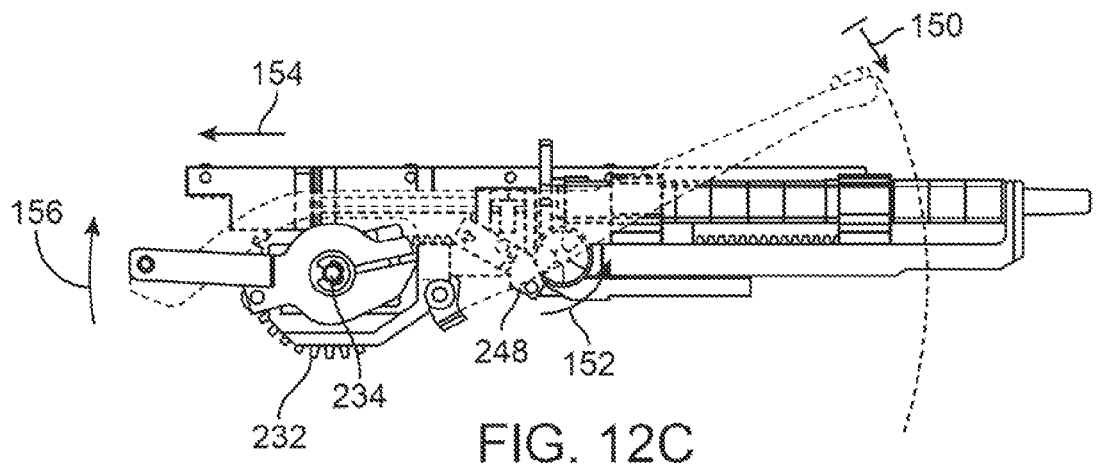

FIGS. 12A to 12E shows an example of the gear drive assembly during movement of the actuator 230 through the first stroke segment 110. FIG. 12A illustrates a rest or initial position of the lever 230. It is noted that the lever as well as other components of the system 100 and/or drive assembly can be spring biased to allow the gears/actuator/etc. to return to an initial position. Continued movement of the lever 230 in direction 150, as shown in FIG. 12B, causes a back drive lever 244 to rotate back drive pulley 236 in direction 152. The back drive pulley 26 is coupled to back drive shaft 236 (shown in FIG. 11A) and rotates back drive gear 236 causing rearward movement of the plunger coupling 242 in direction 154. In the illustrated example, the rear portion 231 of lever 230 has yet to engage main drive lever 244. Once the rear portion 231 of lever 230 engages the main drive lever 248, the main drive lever 248 and rear portion of lever 231 moves in direction 156. However, main drive shaft 234 can employ a one-way clutch such that movement of the lever 244 in direction 156 produces no movement of main gear drive 232. This clutch is necessary since rearward movement of the plunger attachment 242 causes rearward movement of the main rack gear 250.

Figure 12D:
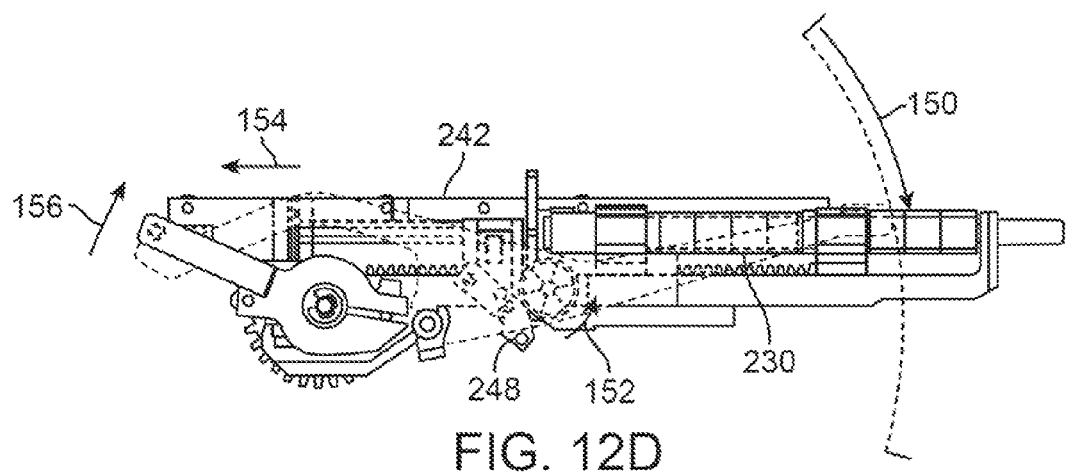
Figure 12E:
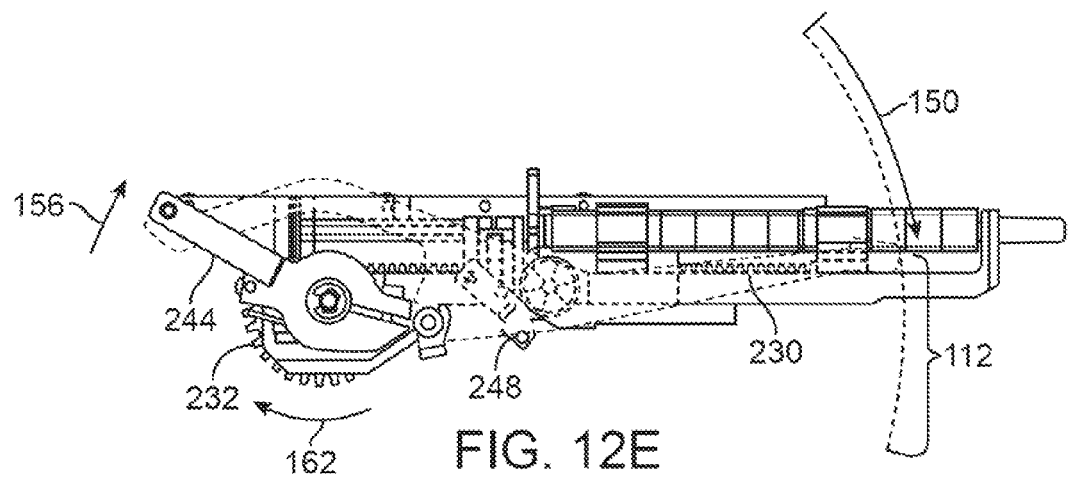
Figure 12F:
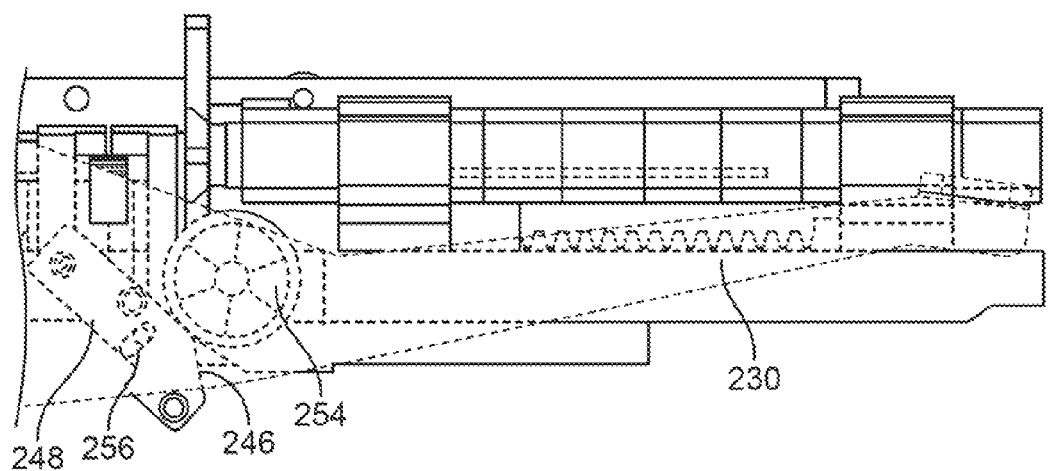
FIG. 12F shows disengagement of the back drive gear mechanism.

FIG. 12D illustrates continued movement of lever 230 and rotation of back drive gear 236 and back drive shaft 238 to continue movement of the plunger coupling 242 in rearward direction 154. FIG. 12E illustrates the condition where movement 150 of lever 230 reaches the second segment 112. In this state, as shown in FIG. 12F, movement 150 of lever 230 into the second segment 112 causes a back drive surface 246 of back drive lever 248 to disengage from back drive pulley 254. In the illustrated example, the slot 256 located in the back drive lever 248 permits movement of the back drive surface 246 away from the back drive pulley 254. However, any number of configurations (such as a cam/follower design, contoured shape, etc., can be used to prevent movement of the back drive pulley 254). Turning back to FIG. 12E, movement of the lever 230 through segment 112 causes continued movement of the main drive lever 244 in direction 156 causing rotation of the first or main gear 232 in direction 162 resulting in advancement of the plunger coupling 242 as the main gear 232 engages the first rack gear 240 (as shown in FIG. 1 IA).

Disengagement prevents rearward movement of the plunger fitting so that continued movement of lever 230 through the second segment 112 causes movement of the first gear 232 and first shaft 234 which ultimately causes forward movement of the plunger fitting and plunger to expel the substance located within the reservoir or barrel. Again, the position of lever 230 is provided for illustrative purposes only and the arc length of the first 110 and second 112 segments can be adjusted based on the amount of negative pressure and amount of fluid delivery required. Moreover, gearing ratios can be adjusted as required to obtain desired displacement or movement of the plunger fitting.

In the sequence described above, the first segment 110 corresponds to a check and the second segment corresponds to delivery of the substance. Clearly, if a medical caregiver observes the presence of blood (or any other negative condition), the caregiver can release the actuator 230 and allow the system to revert to the rest or initial position shown in FIG. 12A if the caregiver is attempting to inject a substance and avoid the muscle. Alternatively, the injection system can be used to confirm delivery of a substance into a vessel where the check can be used to confirm placement of the needle within the vessel. The present disclosure includes any number of permutations of use of the system that allows for movement of a plunger in two directions while minimizing movement of the needle and/or with a single stroke of an actuator.

FIG. 13 shows a bottom view of the variation shown in FIG. 10. The illustrated figure shows an optional lockout feature 258 that has one or more surfaces 260 that can engage a portion of the back drive lever 248 (in this example the lockout feature 258 engages one or more pins 262 of the back drive lever 248). In the illustrated example, the lockout feature 258 can be advanced in direction 158 to engage the back drive lever 248 and disengage the device from performing the check feature.

Figure 14A:
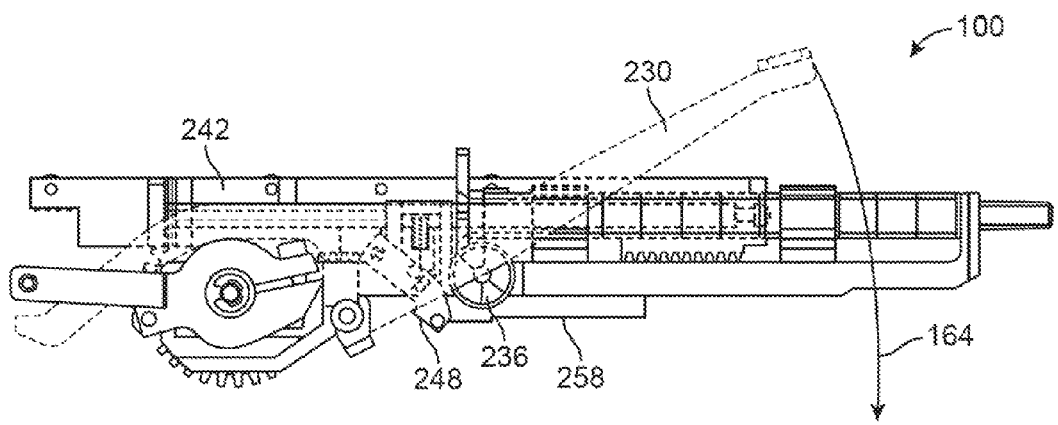
FIGS. 14A to 14C illustrate movement of the actuator to cause advancement of the plunger fitting.
Figure 14B:
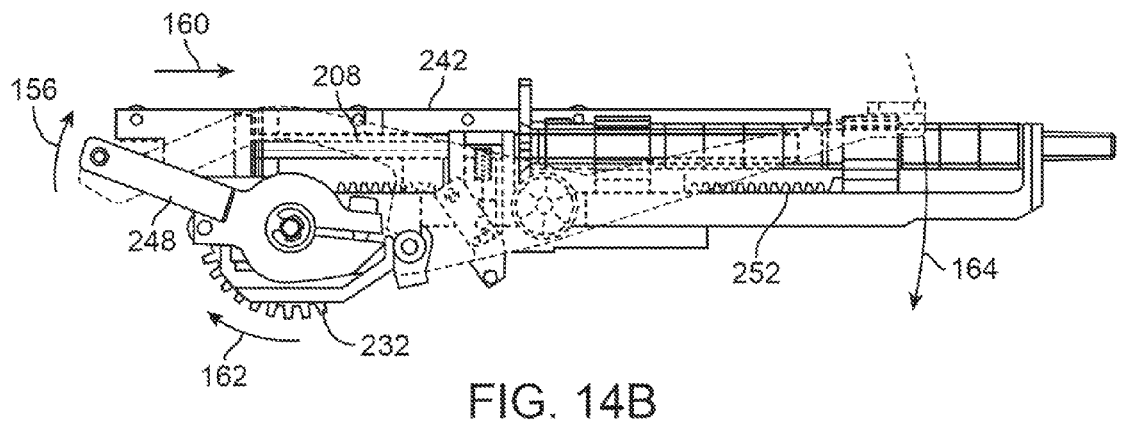
Figure 14C:
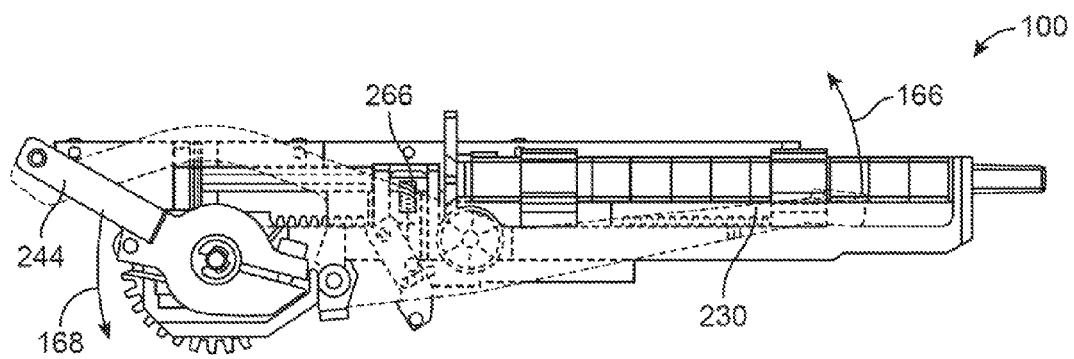

FIGS. 14A to 14C illustrate movement of the actuator 230 to cause advancement of the plunger fitting 242. The examples shown demonstrate the device when the disengagement feature 248 separates the back drive lever 248 from the back drive pulley 236. However, the same principles apply when the back drive arm 248 disengages from the back drive pulley 236 when the actuator 230 enters the second segment 112 of travel as discussed above.

FIG. 14A illustrates the device 100 when the lever 230 is in a rest or initial position and can be moved in direction 164. As shown in FIG. 14B, when lever 230 moves through direction 164, a portion of the actuator engages lever arm 248 and moves lever arm in direction 156. Since there is no counter movement caused by the rear drive pulley 236, main gear 232 moves in direction 162 and engages the main rack gear 252 of the plunger fitting 242 to move the plunger fitting 242 in direction 160. As shown, this causes plunger 208 to move as well. FIG. 14C shows the actuator 230 at the end of a stroke. Again, the position of the actuator 230 relative to the remainder of the device 100 can be varied as needed. Some variations of the invention 100 include a spring reset feature provided by one or more springs 266 that allow the main lever 230 to revert to the initial position shown in FIG. 14A upon removal of an applied force to the lever 230. The spring reset feature also reverts the lever arms 248 244 to their rest positions. In the illustrated example, spring 266 causes movement of actuator 230 in direction 166, where the slot feature can return back drive lever 248 and a second spring (not shown) assists in movement of lever 244 in direction 168.

Figure 15A:
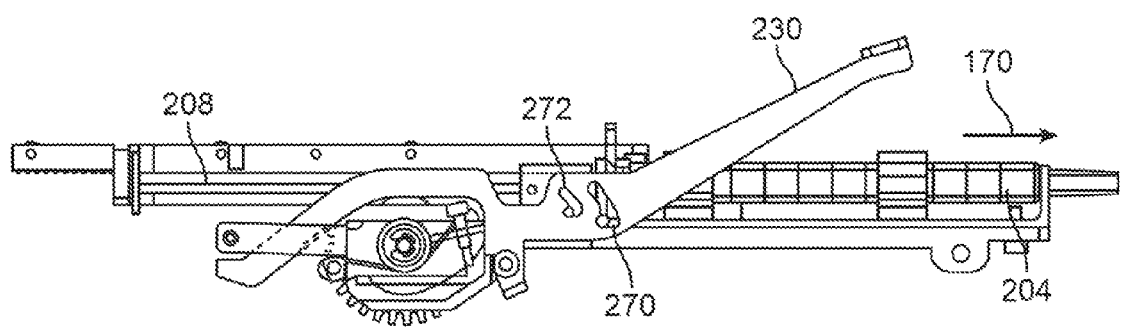
FIGS. 15A and 15B show another variation of a device where the barrel moves relative to the plunger to generate a negative pressure.
Figure 15B:
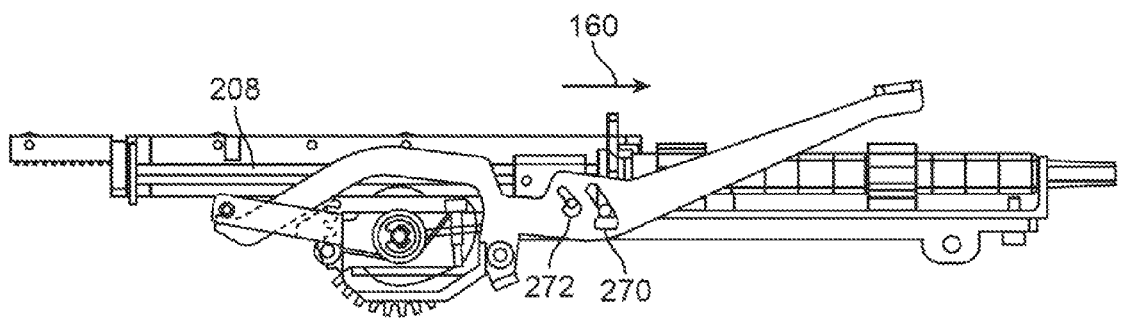

The present disclosure contemplates any number of variations and modification of the devices shown herein that allow for dual movement of a plunger when delivering a substance. For example, FIG. 15A illustrates an alternate design where an actuator 230 moves a barrel 204 in direction 170 while holding the plunger 208 steady where this relative movement creates a negative pressure in the barrel 204 to perform a check function. FIGS. 15A and 15B show one example of a configuration that performs this relative movement where the actuator 230 includes a first and second slots 270 272 that advance the barrel 204 during an initial movement of the lever 230 and then advances the plunger 208 while maintaining the barrel 204 steady so that the plunger advances in direction 160 to dispense the contents of the syringe 204.

Figure 16:
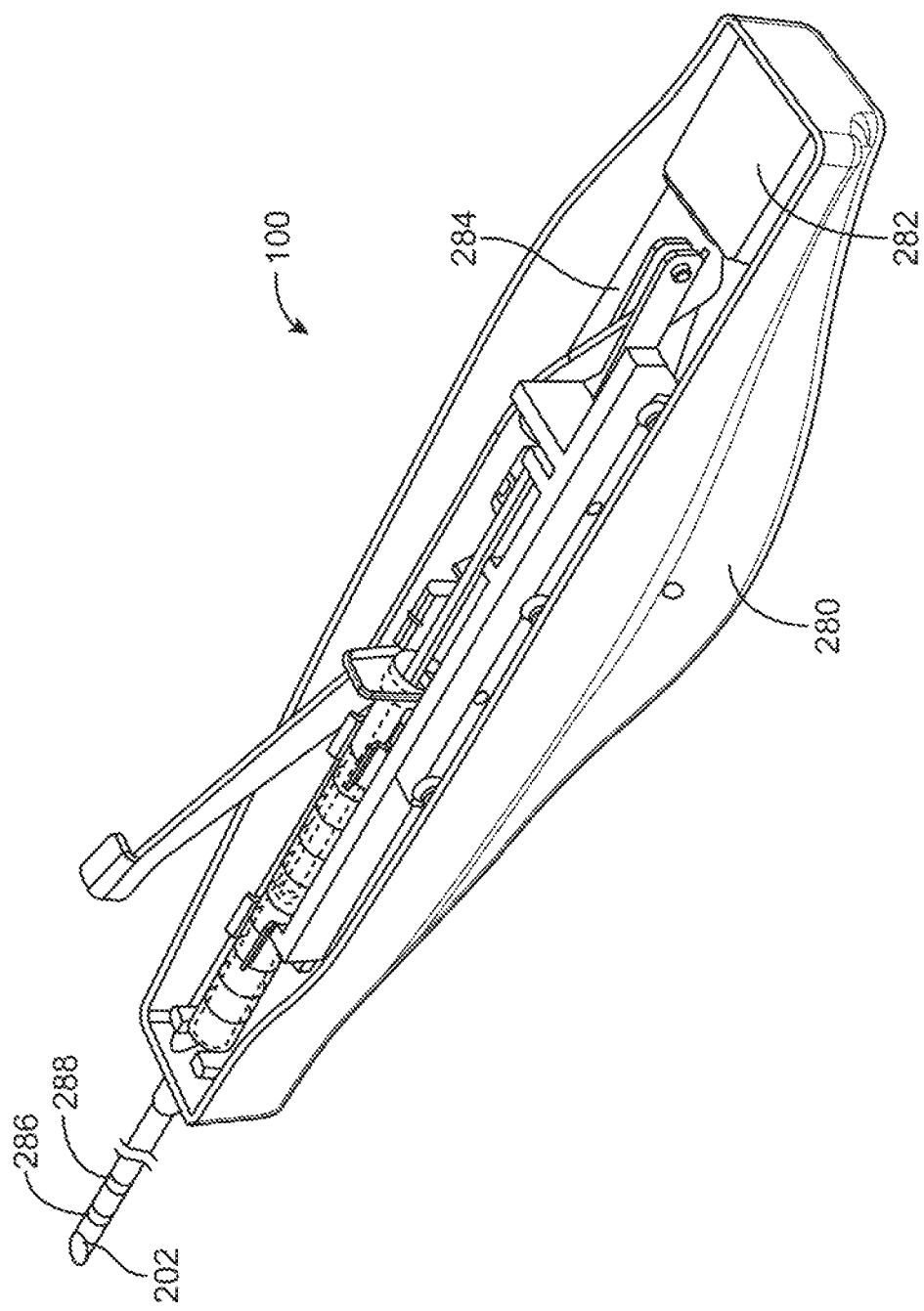
FIG. 16 shows another variation of components for use with the injection systems including a housing and circuitry.

FIG. 16 shows another variation of components for use with the injection systems described herein, as shown, the unit 100 can include any type of outer covering 280 or housing that optionally aids in single handed administration of the device. For purposes of illustration, the housing 280 is shown without a top covering. Furthermore, the housing 280 can include any power supply, electrical contact, memory, or processor (as designated by 282) that can perform sensing through a cannula 202 and/or through any number of electrodes 286, 288 disposed on or in the cannula 202. The circuitry 282 can be coupled to the needle/electrodes 284 using any conventional conductive member 284.

Figure 17:
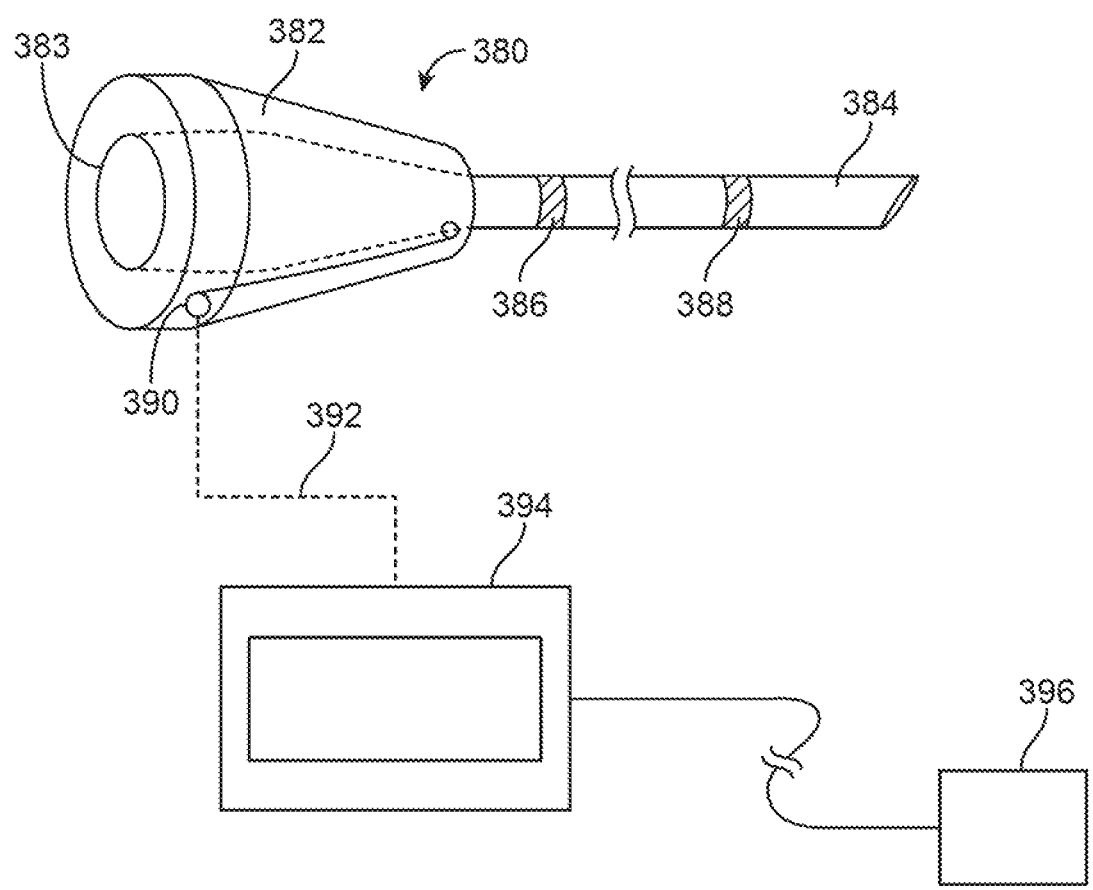
FIG. 17 illustrates another related concept that includes a sensing unit for use with conventional syringes and/or injection systems of the present disclosure.

FIG. 17 illustrates another related concept that can be employed with the injection systems described herein or can be employed as a stand-alone improvement to conventional injection devices that gives a caregiver the ability to determine the type of tissue prior to an injection. As shown, a sensing fitting 380 can include a hub 382 that accepts commercially available syringes, fittings, luers, etc. at an opening 383. The hub 382 can include a conductive cannula 384 and/or one or more electrodes 386, 388. The cannula 384 (and/or electrodes) can be coupled to a fitting 390, shown to be on a hub 382 of the device 380 (but could be located in any location including remotely from the fitting 380), where the fitting allows for coupling of the sensing fitting 380 with a power supply/processor/user interface unit/etc. 394. The unit 394 can include any number of user feedback signals such as audible, visual, graphical displays, etc. Once inserted into tissue, the unit 394 can identify whether the caregiver placed the needle into skin, muscle, fat, blood vessels, etc. As noted above, the needle can be used as part of the current path in either a monopolar mode (where the use of a grounding electrode 396 is required, or in a bi-polar mode with either of the two electrodes in combination with the needle or using the two electrodes alone.

The sensing unit 380 can be used when a caregiver must deliver an injection into a certain tissue (e.g., a vessel, skin, fat, muscle, etc.). The conductive needle 384 (and/or electrodes) can provide electrical current to identify the type of tissue through any known modes of identifying such tissue.

Figure 18:
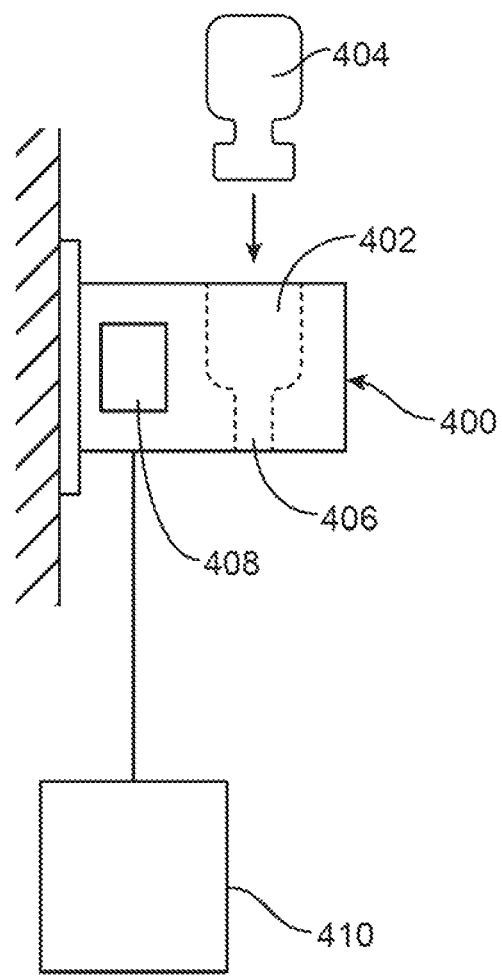
FIG. 18 illustrates another related concept that includes a holding unit for use with conventional syringes and/or injection systems of the present disclosure.

FIG. 18 illustrates yet another aspect for use with the injection systems described herein or with any stand-alone injection system. FIG. 18 shows a holding unit 400 that has an area 402 to accept any type of commonly available vial 402 containing a medicine. The loading unit 400 includes one or more ports 406 for insertion of a needle to draw the substance within a syringe of an injector (not shown). The holding unit 400 is typically coupled to a power supply (either an AC or a DC power supply) that permits the holding unit 400 to maintain the medicine/substance 404 at a desired temperature. Alternatively, the holding unit 400 can include a substance (such as dry-ice, Freon, ice, cold water, hot water, etc.) that can be used to heat or cool the substance 404 without the need for any power supply 410.

Accordingly, the holding unit 400 can include a user interface 408 that provide audible, visual, and/or graphic information regarding the temperature of the substance as well as additional information such as time, batch, type of medicine, etc. The dispensing unit 400 can be affixed to a wall, cart, table, etc. Alternate variations include a portable desktop configuration.

In one example, the dispensing unit shown in FIG. 18 can be used to administer Botox, Xeomin or any similar substance. Such substances are typically reconstituted from a dry lipophilic state. Once reconstituted such substances diminish in potency over time proportional to its temperature. Standard practices include storing reconstituted Botox at a standard temperature of 35 degrees F. The holding unit 400 can prevent having to go to/from freezer/refrigerator when administering. Instead, the holding unit 400 can maintain the vial at the desired temperature allowing for a caregiver to repeatedly access the substance in order to administer injections.

Another added benefit of the holding unit 400 is that the caregiver is able to load a syringe without holding the vial 404 since the vial is temporarily secured within the holding unit 400.

Any feature described in any one embodiment described herein can be combined with any other feature of any other embodiment whether preferred or not.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto.

Although the present methods and devices have been described in terms of the embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims of the invention.

What is claimed is:

1. A dispensing unit for use with a syringe, the syringe having a barrel, and a plunger slidable relative to the barrel to dispense substances located therein, the medical dispensing system comprising:
   a housing assembly being configured to secure the barrel such that a distal end of the barrel is adjacent to a distal end of the housing assembly;
   a drive mechanism coupled to the housing assembly, the drive mechanism comprising a plunger fitting that engages the plunger;
   an actuator; and
   a gear drive assembly being coupled between the plunger fitting and the actuator, the gear drive assembly being configured to move in response to a single directional movement of the actuator to produce movement of the plunger fitting in a first direction relative to the distal end of the housing and subsequently in a second direction that is opposite to the first direction during single directional movement of the actuator.

2. The dispensing unit of claim 1, where the first direction comprises a rearward direction relative to the distal end and the second direction comprises a forward direction relative to the distal end.

3. The dispensing unit of claim 1, where a portion of the gear drive assembly can disengage such that the plunger fitting moves in the second direction in the single directional stroke of the actuator.

4. The dispensing unit of claim 1, where the gear drive assembly comprises at least a first gear structure configured to produce movement of the plunger fitting in the rearward direction and a second gear structure configured to produce movement of the plunger fitting in the forward direction; and
   where the single directional movement of the actuator comprises a first segment and a second segment, where movement of the actuator in the first segment causes movement of the first gear structure and movement of the actuator in the second segment causes movement of the second gear structure.

5. The dispensing unit of claim 4, where the gear drive assembly disengages the first gear structure during movement of the actuator in the second segment.

6. The dispensing unit of claim 4, where the first gear structure comprises a rack and pinion assembly.

7. The dispensing unit of claim 4, where the second gear structure comprises a rack and pinion assembly.

8. The dispensing unit of claim 4, where the first gear structure is releasably coupled to the actuator through a first shaft such that movement of the actuator through the first segment to the second segment causes de-coupling of the first shaft and actuator.

9. The dispensing unit of claim 4, where the second gear structure is disengaged from the actuator until the actuator moves through the first segment.

10. The dispensing unit of claim 4, where the second gear structure is coupled to the actuator through a second shaft.

11. The dispensing unit of claim 1, where the actuator is coupled to a first shaft that is rotatably relative to the housing assembly, where a portion of the first shaft is coupled to the gear drive assembly.

12. The dispensing unit of claim 11, where the first shaft is located proximal to the barrel.

13. A dispensing unit for use with a syringe, the syringe having a barrel, and a plunger slidable relative to the barrel to dispense substances located therein, the medical dispensing system comprising:
   a housing assembly being configured to secure the barrel;
   a drive mechanism coupled to the housing assembly, the drive mechanism comprising a plunger fitting that engages the plunger;
   an actuator configured to move rotationally in a single direction through a stroke, the stroke comprising a first segment and a second segment; and
   a gear drive assembly being coupled between the plunger fitting and the actuator, the gear drive assembly being configured to move in response to movement of the actuator through the stroke to produce movement of the plunger fitting in a first direction during the first segment of the stroke and subsequently in a second direction that is opposite to the first direction during the second segment of the actuator stroke.

14. The dispensing unit of claim 13, where the first direction comprises a rearward direction relative to the distal end and the second direction comprises a forward direction relative to the distal end.

15. The dispensing unit of claim 13, where a portion of the gear drive assembly is configured to disengage such that the plunger fitting moves in the second direction during movement of the actuator.

16. The dispensing unit of claim 15, where the gear drive assembly disengages the first gear structure during movement of the actuator in the second segment.

17. The dispensing unit of claim 16, where the first gear structure is releasable coupled to the actuator through a first shaft such that movement of the actuator through the first segment to the second segment causes de-coupling of the first shaft and actuator.

18. The dispensing unit of claim 16, where the second gear structure is disengaged from the actuator until the actuator moves through the first segment.

\* \* \* \* \*